US012036233B2

(12) United States Patent
Grentzmann et al.

(10) Patent No.: US 12,036,233 B2
(45) Date of Patent: Jul. 16, 2024

(54) CARBOHYDRATE COMPOSITION FOR DIALYSIS

(71) Applicant: OPTERION Health AG, Muttenz (CH)

(72) Inventors: Guido Grentzmann, Hamburg (DE); Hjalmar Steinhauer, Cottbus (DE)

(73) Assignee: OPTERION HEALTH AG, Muttenz (CH)

( * ) Notice: Subject to any disclaimer, the term of this patent is extended or adjusted under 35 U.S.C. 154(b) by 0 days.

(21) Appl. No.: 15/780,214

(22) PCT Filed: Mar. 22, 2018

(86) PCT No.: PCT/EP2018/057275
§ 371 (c)(1),
(2) Date: May 30, 2018

(87) PCT Pub. No.: WO2018/146345
PCT Pub. Date: Aug. 16, 2018

(65) Prior Publication Data
US 2020/0397814 A1  Dec. 24, 2020

(30) Foreign Application Priority Data
Mar. 31, 2017 (EP) .................... 17164425

(51) Int. Cl.
A61K 31/716 (2006.01)
A61K 47/26 (2006.01)
A61M 1/28 (2006.01)
A61K 9/08 (2006.01)

(52) U.S. Cl.
CPC ............ A61K 31/716 (2013.01); A61K 47/26 (2013.01); A61M 1/287 (2013.01); A61K 9/08 (2013.01)

(58) Field of Classification Search
CPC .......................................... A61K 31/716–722
See application file for complete search history.

(56) References Cited

U.S. PATENT DOCUMENTS

| | | | |
|---|---|---|---|
| 4,182,756 A | 1/1980 | Ramsay et al. | |
| 4,879,280 A * | 11/1989 | Seyffart | A61K 31/70 514/53 |
| 4,886,789 A | 12/1989 | Milner | |
| 6,077,836 A | 6/2000 | Milner | |
| 6,248,726 B1 | 6/2001 | Alsop et al. | |
| 6,306,836 B1 | 10/2001 | Martis et al. | |
| 2004/0014961 A1* | 1/2004 | Backer | A61M 1/287 536/123 |
| 2012/0238525 A1 | 9/2012 | Eypoldt et al. | |
| 2012/0295873 A1 | 11/2012 | Guerin-Deremaux et al. | |

FOREIGN PATENT DOCUMENTS

| | | |
|---|---|---|
| CN | 105524181 A | 4/2016 |
| EP | 0076355 A2 | 4/1983 |
| EP | 0115911 A1 | 8/1984 |
| EP | 3381484 A1 | 10/2018 |
| GB | 2042547 A | 9/1980 |
| RU | 2118531 C1 | 9/1998 |
| WO | 8300087 A1 | 1/1983 |
| WO | 9519778 A1 | 7/1995 |
| WO | 2004058277 A1 | 7/2004 |
| WO | 2007128559 A2 | 11/2007 |
| WO | 2017013120 A1 | 1/2017 |

OTHER PUBLICATIONS

Leypoldt, J. et al "Ultrafiltration characteristics of glucose polymers . . . " Periton. Dial. Int., vol. 33, pp. 124-131. (Year: 2013).*
Garcia-Lopez, E. et al "An update on peritoneal dialysis solutions" Nat. Rev. Nephrol., vol. 8, pp. 224-233. (Year: 2012).*
Nikitidou, O. et al "Animal models in peritoneal dialysis" vol. 6, art. 244, pp. 1-5. (Year: 2015).*
Davies, Donald S.: "Kinetics of Icodextrin", Scientific Symposium in Icodextrin in PD, 1993, London. UK, pp. S45-S50.
De Waart, et al.: "Icodextrin Degradation Products in Spent Dialysate of Card Patients and the Rat, and Its Relation With Dialysate Osmolality", Peritoneal Dialysis International 21 (2001), pp. 269-274.
Dousdampanis, et al.: "Bimodal Solutions or Twice-Daily Icodextrin to Enhance Ultrafiltration in Peritoneal Dialysis Patients", Int'l J. of Nephroloty (2013), pp. 1-6.
Frieda, et al.: "The contribution of combined crystalloid and colloid osmosis to fluid and sodium management in peritoneal dialysis", Kidney International 73 (2008), pp. S102-S111.
Moberly, et al.: "Pharmacokinetics of icodextrin in peritoneal dialysis patients", Kidney International 62 (81), (2002), pp. S23-S33.
Kratkaya Khimicheskaya Entsiklopediya (EN: Brief Chemical Encyclopedia) vol. 1 "A-E", Chief Editor I. L. Knunyants, Publ. "Sovetskaya Entsiklopediya" (EN: Soviet Encyclopedia), Moscow, (1961), p. 180.
Yakubke. et al.: "Amino acids Peptides Proteins", Translation from German Language, ed. by Yu. V. Mitina, Publ. "Mir", Moscow (1985), pp. 9-23.
Mistry, et al.: "Glucose Polymer As an Osmotic Agent in CAPD", in Frontiers in Peritoneal Dialysis, Milner, et al. (eds), (1986), Springer-Verlag Berlin Heidelberg, pp. 241-248.
Winchester, et al.: "A Comparison of Glucose Polymer and Dextrose as Osmotic Agents in CAPD", in Frontiers in Peritoneal Dialysis, Maher et al. (eds.), (1986), Springer-Verlag Berlin Heidelberg, pp. 231-240.
Leypoldt, J.K. et al., "Ultrafiltration characteristics of glucose polymers with low polydispersity", Peritoneal Dialysis International, vol. 33, pp. 124-131, 2013.
Mistry, C.D. et al., "Clinical Studies of new Icodextrin Formulations", Peritoneal Dialysis International, vol. 14, Suppl. 2, 1994.
Mistry, C.D. et al, "Optimal use of glucose polymer (Icodextrin) in peritoneal dialysis", Peritoneal Dialysis International, vol. 16, 1996, Supplement 1.
Gokal, R. et at., "Osmotic agents in continuous ambulatory peritoneal dialysis", Nefrologoa, vol. VIII No. 3. 1988, 118-121.

(Continued)

Primary Examiner — Leigh C Maier
(74) Attorney, Agent, or Firm — ArentFox Schiff LLP

(57) ABSTRACT

Carbohydrate compositions for dialysis and methods of making and using them are provided.

20 Claims, No Drawings

(56) References Cited

OTHER PUBLICATIONS

Jenkins, S. et al., "Mixing osmotic agents—two different approaches", Peritoneal Dialysis International, vol. 27, pp. 245-250, 2007.
Freida, P. et al., "Combination of crystalloid (glucose) and colloid (icodextrin) osmotic agents markedly enhances peritoneal fluid and solute transport during long PD dwell", Peritoneal Dialysis International, vol. 27, pp. 267-276, 2007.
Opposition against EP3600486B1, dated Nov. 16, 2021, in corresponding European Patent No. EP3600486B1.
Frampton et al., "Icodextrin: a review of its use in peritoneal dialysis." Drugs. 2003;63(19):2079-105.
Garcia-Lopez et al., "Determination of high and low molecular weight molecules of icodextrin in plasma and dialysate, using gel filtration chromatography, in peritoneal dialysis patients." Perit Dial Int. Mar.-Apr. 2005;25(2):181-91.
Li et al., "The effect of starch concentration on the gelatinization and liquefaction of corn starch." Food Hydrocolloids. 2015;48:189-196.
Olsen, "Enzymatic production of glucose syrups." In: Kearsley, M.W., Dziedzic, S.Z. (eds) Handbook of Starch Hydrolysis Products and their Derivatives. Springer, Boston, MA. 1995;26-64.
Summons to Attend to Oral Proceedings from the European Patent Office dated Jul. 14, 2022 issued in a counterpart foreign application No. 18714471.2.
Garcia-Lopez et al., "An update on peritoneal dialysis solutions." Nat Rev Nephrol. Feb. 21, 2012;8(4):224-33.

\* cited by examiner

CARBOHYDRATE COMPOSITION FOR DIALYSIS

FIELD OF THE INVENTION

The present invention relates to an osmotically active composition, to an aqueous solution comprising such composition and to the uses thereof.

BACKGROUND OF THE INVENTION

Specifically in the area of peritoneal dialysis, many works have been accomplished, describing most different osmotically active compositions, including saccharide polymer preparations, and their dialysis parameters in the clinic or in animal models, and different measurement methods have been applied to establish parameters of their compositions. A very well described medically applied saccharide polymer preparation for medical application is Icodextrin.

Permanent dialysis treatment still causes significant side-effects, by interaction between dialysis material (tubes, dialysis materials and solutions) and patient tissues.

Hemodialysis (HD) is the most commonly applied dialysis treatment. Respective side-effects include inflammatory and cardiovascular complications, causing increased death rates.

Peritoneal dialysis (PD) represents an alternative to extracorporal hemodialysis. It has the advantage of being independent from heavy instrumentation, and can be done at home. Furthermore, PD does not require drawing the patient's blood out of the body. Instead, the process uses the patient's peritoneal capillary tissue as a membrane, exchanging fluids and dissolved substances (electrolytes, urea, glucose, and other small molecules) between blood and the dialysate. A PD-Fluid (hereinafter: PDF) is introduced through a permanent tube into the abdomen and, at the end of the peritoneal dialysis dwell, flushed out. Such dwells may be carried out repeatedly, for various durations, at different time intervals. Maybe the most important advantage of PD is, that it preserves residual kidney activities significantly, as compared to hemodialysis (HD). This is not only of advantage to the patient allowing excretion of certain amounts of body fluid by natural ways, but is also of high advantage to peritoneal dialysis treatment itself, allowing a significant amount of excretion of slowly metabolizable, small molecular weight components from peritonea dialysis fluids.

Common PDFs use glucose as osmotic agent at concentrations between 1 and 5%, to achieve transfer of fluid and toxic agent out of the blood into the dialysate. Glucose is a low molecular weight constituent of blood (normal concentration around 0.1%). High glucose concentration of conventional PDFs leads to back diffusion of glucose, from the dialysate into the patient's blood stream, generating glucose overcharge, which is able to provoke hyperglycemia. Hyperglycemia is specifically problematic, since many dialysis patients are diabetic.

One way to address this problem is the use of saccharide polymers as an alternative osmotic agent to replace glucose. Prior art of described polysaccharide is provided above.

The general advantage of glucose polymers is, that in the peritoneum, and in the blood, they are not catabolized to glucose, but only to maltose and maltotriose. Both these molecules are significantly less metabolized by the body, and are, to a large extend excreted through residual renal function and/or through back dialysis into the dialysate of a next dwell.

Another advantage, specifically of poly-glucoses based PDFs is, that these solutions maintain their own osmotic pressure. At the same time as some osmotic material gets lost by resorption through the body, intraperitoneal amylases cut the polymer into smaller saccharides, thereby increasing the osmotic pressure of the remaining intraperitoneal maltodextrins. As a result, polysaccharide based PDFs can be administered at low osmolality and will continue fluid resorption through ultrafiltration for many hours.

In 1986, Mistry et al. and Winchester et al., independently describe PDFs containing glucose polymers in "Frontiers in Peritoneal Dialysis, eds: John F. Maher M.D., James F. Winchester M.D., 1986, Springer Verlag, Heidelberg). Mistry describes a polymer preparation containing glucose polymers of DP 1 to 10, Winchester describes a polymer preparation with molecules of DP<6 of less than 5 wt-%.

EP 0115911 discloses glucose polymers containing more than 15% of molecules of DP>12 wherein said preparation show an Mw 7-36 kD, preferred 15-25 kD.

WO 8300087 A1 discloses glucose polymer preparations of an average DP of 4 to 10.

EP 0076355 A2 discloses glucose polymer preparations for peritoneal dialysis containing at least 85 wt-% of molecules less than DP 11, and at least 99 wt-% of molecules of less than DP 26.

U.S. Pat. No. 4,182,756 B1 discloses a substantially clear, nonpyrogenic, stable and sterile solution for intravenous administration to human patients, said solution comprising at least 20% W/V of a glucose polymer mixture having an average degree of polymerization of at least 4 and at least 99% of its molecules less than 26 glucose units, at least 85% of its molecules less than 11 glucose units, and at least 20% of its molecules less than 4 glucose units.

U.S. Pat. No. 6,248,726 B1 discloses a glucose polymer mixture, wherein at least 50% by weight of the polymer is of molecular weight in the range 5000 to 30000, wherein at least 80% by weight of the polymer is of molecular weight in the range 5000 to 50,000, wherein a weight average molecular weight in the range of from 5000 to 100000, wherein a number average molecular weight of less than 8000, and wherein the content of mono-, di-, and tri-saccharide compounds present in the glucose polymer to be less than 5% by weight, and wherein the content of glucose polymers with molecular weight greater than 100000 in the glucose polymer is less than 5%.

GB 2 042 547 discloses starch hydrolysates, which optionally maybe hydrogenated, whose glucid spectrum displays: a content of monosaccharides (DP=1) of less than 14%, a content of disaccharides (DP=2) of less than 35%, a content of oligosaccharides of DP 4 to DP 10 in the range of from 42% to 70%; and a content of polysaccharides of DP greater than 10 of less than 32%; all said percentages being percentages by weight, calculated on the basis of dry matter.

Until now, high average molecular weight of saccharide polymers are used as osmotic agents in PD, to reduce carbohydrate (hereinafter also abbreviated as: CHO) back diffusion from the dialysis fluid into the blood of the patient. The drawback of such high molecular weight polymer osmotic agents is that high MW molecules generate less osmotic pressure than the same percentage of low MW molecules. A solution's osmolality decreases as the size of the osmotic active polymers increases (for a given w/v concentration). In order to obtain comparable osmotic pressure, one has therefore to increase in the CHO concentration. For example, Icodextrin at 7.5% in a physiological salt solution is barely above physiological osmolality and speed of fluid ultrafiltration is slow. Due to a relatively constant absorption of dialysate from the peritoneum through the lymphatic system, a high carbohydrate uptake during the dialysis dwell is the consequence. Despite this fact, recent new developments look for even higher molecular weights of polysaccharides in PDFs, such as US2012/02385A1.

Average osmolality of human blood is between 275 and 295 mOsm/kg, and is due to major solutes in the blood, such as salts, other low molecular weight solutes and proteins. Peritoneal fluids contain the major salts found in blood, as well as a pH buffer, but generally no proteins. In any peritoneal treatment an osmotic pressure near to the human blood osmolality is necessary to avoid rapid absorption of the peritoneal liquid into the body. In peritoneal dialysis, one eventually needs to exceed the osmolality of blood, in order to generate a fluid transfer from the patient's blood circulation compartment into the dialysis fluid compartment. The necessary osmotic pressure in peritoneal therapeutic fluids (PTFs) and peritoneal dialysis fluids (PDFs) is achieved by addition of "osmotic agents". Examples for osmotic agents are glucose and maltodextrin or other mono- and/or polymeric saccharide molecules, amino-acids, cyciodextrins, PEGs, derivatives of such compounds and mixtures of such compounds and/or their derivatives. Osmotic pressure of a solution may be measured in mOsm/kg. Currently marketed PDFs are applied at osmolalities between 280 and 500 mOsm/kg.

Extraneal®, is the only polysaccharide containing PDF marketed today. It contains icodextrin, a maltodextrin with an Mw of 13 to 16 kD and an Mn of 5 to 6.5 kD (resulting in a Poly-D of approximately 2.8). Extraneal® has a CHO concentration of 7.5%, necessary to reach iso-osmolality with human blood and to initiate ultrafiltration. Upon instillation into the peritoneal cavity, osmolality evolves to values between 290 and 325 mOsm/kg (De Wart et al. 2001. Peritoneal Dialysis International, Vol. 21, pp. 269-274), within 8 to 12 hours, although the dialysate volume increases slowly, and although average absorption of 30 to 40% of icodextrin into the body has been reported during the dialysis dwell (Davies. Kinetics of icodextrin. Perit Dial Int 1994; 14 (Suppl 2): S45-50; Moberly et al. 2002. Kidney International, Vol. 62, Supplement 81 (2002), pp. S23-S33). Progressive digestion of icodextrin is occurring as well in the peritoneum as in the blood stream by low concentrated amylases (Moberly et al. 2002).

A major disadvantage of Icodextrin is the very slow ultrafiltration, and therefore 8 to 12 hour dwells are usually applied. Therefore, in most cases, Extraneal® cannot be applied as a monotherapy, but only as a once-a-day dialysis application of 8 to 12 hours, and the use of Icodextrin in automated dialysis has also been questioned (Freid et al. 2008). Short dialysis dwells to efficiently reduce body fluid, today, are therefore carried out applying glucose-based PDFs in most cases.

So far Extraneal® is generally applied once a day, and only experimentally or exceptionally twice a day, because of the long dwell time and of concerns of polysaccharide absorption.

An experimental glucose polymer preparation was described by Leypoldt et al. (2013, Perotoneal Dialysis International, Vol. 33, pp 124-131) having Mw of 6.4 kD the Mn 2.8 kD. The authors fractionated Icodextrin, in one low average molecular weight preparation (weight average molecular weight Mw 6.4 kD, number average molecular weight Mn 2.8 kD) and one high molecular preparation (Mw 18.8 kD, Mn9.4 kD). Both preparations were tested, at the concentration of 7.5%, in a rabbit model with permanent catheters. The authors suggest, in this model, that a 240 min dwell corresponds to a long dwell in PD patients. In this publication the authors report NUF for the low molecular weight fraction between roughly 60 and 85 ml, and NUF for the high molecular weight fraction between roughly 40 and 45 ml, for an initial dialysate volume of 100 ml, after a 240 min dwell, and conclude that a low molecular weight glucose polymer is more effectively generating UF and produces a higher UF efficiency, those factors come at the expense of the polymer being more readily absorbed from the peritoneal cavity. No results on concentrations lower than 7.5% were reported. No NUF Volumes for shorter delays than 240 minutes were reported.

Although there was a difference between the low Mw Fraction and the high Mw fraction, no data comparing the low molecular weight solution and Icodextrin was reported.

Finally, to increase Icodextrin PDF solution osmotic efficacy, bimodal PDFs have been made, combining Icodextrin with glucose, but then again such solution were not glucose free any longer (Dousdampanis et al. 2013, Internat. J. of Nephrology, Vol. 2013, Article ID424915, Freida et al. 2008, Kidney International Vol. 73, p S102-S111).

OBJECTIVE OF THE INVENTION

The objective of the invention was to provide with a composition, that fulfils one or more of the following functions:
shows higher osmolality than Icodextrin, at lower carbohydrate concentration
increases net ultra filtration as compared to icodextrin, at such lower carbohydrate concentration.
enables reasonable net ultrafiltration during short dialysis dwells (particularly 2 to 4 hours in humans).
shows a higher ratio of Net-Ultrafiltration Volume over carbohydrate absorption at such reduced carbohydrate concentrations, as compared to Icodextrin.
contains glucose at a final concentration of less than 0.2% w/v of the final solution.
contains a sufficient concentration of high molecular weight components to sustain positive osmotic pressure during the entire dwell.

SUMMARY OF THE INVENTION

The present invention provides with a composition, comprising or consisting of:
a) a compound that is selected from the group consisting of maltose, glycerol, an amino acid, an oligopeptide, or a mixture of one or more thereof, preferably maltose, in a content of 5 to 75 wt-% of the total weight of a)-d), preferably 8-65 wt-%, more preferably 10-55 wt-%,
b) glucose in a content of less than ½, preferably less than ⅓, the content of a), and in a total content of less than 5 wt-% of the total weight of a)-d),
c) glucan molecules of DP 3 and DP 4, taken together, in a content of less than ½, preferably less than ⅓, of the content of a),
d) glucan molecules of DP>4 in a content to give 100 wt-% together with a), b) and c), wherein
glucan molecules of DP>10 are present in an amount of 15-85 wt-%, preferably 20-80 wt-%, further preferably 35-80 wt-%, of the total weight of a)-d),
glucan molecules of DP>24 are present in an amount of 2-60 wt-%, preferably 4-58 wt-%, more preferably 5-56 wt-% of the total weight of a)-d), glucan molecules of DP>55 are present in an amount of less than 15 wt-% of the total weight of a)-d), preferably less than 12 wt-%, more preferably.

The weight average molecular weight of a)-d), taken together, may be Mw 0.8-15 kD, preferably Mw 1.0-10 kD, more preferably Mw 1.2-6.2 kD or 1-6.2 kD, more preferably 1.4-6 kD, more preferably 1.6 to 5.8 kD The number average molecular weight of a)-d), taken together, may be Mn 0.2-3 kD, preferably Mn 0.3-3 KD, more preferably Mn 0.5-3 kD or 0.7-3 kD, preferably 0.8-2.7 kD, more preferably 0.9-2.6 kD.

These Mw and Mn values can be combined in any combination, for example Mw 1-6.2 kD and Mn 0.7-3 kD.

Maltose may be used singly in a). Maltose may be partly or completely replaced by other low $M_w$ molecules that do not impact insulin secretion, such as mentioned amino-acids, oligopeptides, and/or glycerol. Such compounds are presently applied examples for low molecular weight osmotic agents.

Features indicated with the attribute "preferably", "more preferably", "even more preferably" etc. can be combined in any combination, also with features not indicated with any of these attributes. For example, a feature indicated with the attribute "preferably" may be combined with a feature not comprising any of such attributes, or with a feature comprising the attribute "more preferably" etc.

The sign "-" in connection with numbers and units indicates ranges, if not otherwise indicated.

The invention also provides with a liquid aqueous composition, comprising such composition and water.

In a further aspect the invention provides with said composition or said liquid aqueous composition for use as a medicament or for use in therapy, wherein specific uses are mentioned in the detailed description.

The invention also provides with a method for producing a liquid aqueous composition as mentioned above, comprising
  preparing an aqueous solution of starch, having a solids content of from 10 wt-% to 60 wt-% by weight;
  gelatinization, by treating said solution successively with a specific combination of enzymes chosen from amyloglucosidase and/or amylase,
  purifying the solution,
  fractionating the solution in such a way as to eliminate or decrease molecular-weight saccharide fractions having a molecular weight higher than 40000 D, preferred higher than 18 kD, and to recovering the other fractions,
  adding a compound that is selected from the group consisting of maltose, glycerol, an amino acid, an oligopeptide, or a mixture of one or more thereof, and optionally glucose, Thereby, particularly by fractionation and by addition of maltose, glycerol, amino-acids or oligo-peptides, optionally glucose, a composition of the invention is obtained, or obtained in the solution.

The invention also provides with a container or kit comprising at least one compartment, containing a liquid aqueous composition as mentioned above or a composition of the invention.

One or more of the following benefits can be reached with the present invention, in the general or in specific embodiments
  The composition show osmotical activity. In this sense the composition is also called osmotically active composition
  the liquid composition contains no more glucose than the physiological level (0.2% max)
  highly reduced fractions of saccharide with high molecular weight (above 40 kD, further preferred above 18 kD),
  a composition of lower average molecular weight than Icodextrin. The composition, as compared to icodextrin, has significantly reduced high molecular weight saccharides, above 18 and 40 kD respectively.
  Cytotoxic effects of Icodextrin on primary human mesothelial cell-cultures are reduced. It is believed that such cytotoxic effects at least partly related to high molecular weight saccharide fractions of Icodextrin. The present invention excludes or reduces potentially cytotoxic, high molecular weight fractions (preferably higher 40 kD of less than 0.6 wt-%, preferred less than 0.3 wt-%, even more preferably higher 18 kD less than 1.5%, of the entire composition.
  the composition of the invention, if applied as the sole osmotic agent to PTFs or PDFs in the presence of physiologic concentration of salts, is able to generate iso-osmolality or to generate hyper-osmolality (higher than physiological Osmolality of human blood) at concentrations of 2-7.2% total CHO (w/v), preferably 2.2 and 7%, preferably 2.4 to 6.8%, preferably 2.6 to 6.6% total CHO (w/v).

In accordance with this invention, a composition is provided, acting as an osmotic agent, in medical applications, preferred PTFs, preferred PDFs. The composition, alone, or together with a low molecular weight osmotic agent, is able to generate sufficiently high osmolality to cause diffusion of water and waste products across the peritoneum after infusion of the peritoneal dialysis fluid into the peritoneal cavity of a patient. In addition to one osmotic agent, or to a combination of osmotic agents, such a medical application fluid contains amounts of various physiologically important electrolytes, comparable to those in human body fluids.

As compared with a currently applied maltodextrin (icodextrin) in a commercialized PDF (Extraneal®, Baxter), in terms of osmotic agent efficacy, the composition of the invention and their derivatives can surprisingly be distinguished from Icodextrin by one or more of the following effects:
  a significantly increased transcapillary ultrafiltration (TCUF) during short dwells. TCUF is defined in the detailed description.
  a significantly increased net-ultrafiltration (NUF) during short dwells. NUF is defined in the detailed description.
  a significantly increased TCUF per unit of time (ml/h).
  a significantly increased NUF per unit of time (ml/h).
  a significantly increased TCUF per unit of carbohydrate (CHO) absorption (ml/g).
  a significantly increased NUF per unit CHO concentration (ml/g).
  lower overall CHO concentration in the PDF.

The results obtained in the frame of this invention suggests the possibility of applying our solution twice, three or four times a day, because of shortened dwell time, lower CHO concentration and the resulting decreased CHO absorption per dwell. Such increased ultrafiltration shall allow, in certain cases, saccharide-polymer based PD as a monotherapy. An increased part of saccharide polymer-based PD during the day would be of great benefit, further reducing current problems of hyperglycemia, in the case of diabetic PD patients.

In accordance with this invention, compositions of the invention enhance ultrafiltration efficacy as described above because of the following characteristics
a) being an efficient osmotic agent during short dialysis dwells
b) having a high reservoir of cleavable bonds to allow maintenance of osmolality during long dwells.

Definitions

For description of concentrations of dissolved solid components of a solution (e.g. a glucose polymer mixture in a peritoneal dialysis solution), in this patent application, it was applied Volume percentage (% w/v) corresponding to an amount by weight of a given compound by volume of solution, e.g. 10% w/v corresponds to 10 g of referred compound in 100 ml of final solution, which corresponds to a commonly applied standard in pharmacological descriptions of such solutions.

In this application the term "glucan" means any composition or polydisperse mixture of oligomeric and/or polymeric molecules (=glucan molecules) consisting of D-glucose monomers, wherein the D-glucose monomers are linked by glycosidic bonds. Instead of the term "glucan" the term "glucose polymer" may be used. The degree of polymerization (DP) of the glucan molecules is per definition in the present invention at least 3. A dimer (DP 2) is called in the present invention "maltose", the monomer is called "glucose", wherein these terms have the known meaning.

The glucan of the invention is preferably an "α-glucan". The term "α-glucan" means a glucan wherein the D-glucose monomers are linked by a-glycosidic bonds.

The term "dextrin" means a glucan comprising α-1,4 and/or α-1,6 glycosidic bonds, preferable both. Dextrins may include maltodextrins and cyclodextrins. A dextrin may be obtained, without limitation, by starch hydrolysis or any other procedure. A special dextrin is icodextrin or starch hydrolysis products of molecular weights between 180 Daltons and 200 kilo-Daltons (kD).

The term "maltodextrin" means a dextrin not comprising cyclodextrins. In a special case maltodextrin is icodextrin, or other linear or branched non-cyclic dextrins of molecular weights between 180 Daltons and 200 kilo-Daltons. Maltodextrins can be generated from limited hydrolysis from starch. Starch is composed from two kinds of glucose polymers: amylose, which are straight chains of glucose polymers bound by α(1,4) glycosidic bonds, and amylopectin containing around ten percent of α(1,6) glycosidic bonds, introducing branching into the saccharide polymer. As a result of initial composition of the starch, of conditions of hydrolysis, or of addition of specific enzymes, the resulting maltodextrin may have different degrees of branching (for example between 0 and 40%).

The term "dextran" means an α-1,6-glucan with α-1,3-branches.

The term "derivative" of a glucan or glucan molecule or "derivatized" means modified molecules or molecule populations derived from enzymatic, chemical and/or physical modification. For example, polymers bonds may be hydrolyzed or supplementary bonds may be generated, or functional groups in the glucan, particularly hydroxyl groups may be derivatized or substituted.

Starch derivatives mean modified starches derived from the enzymatic, chemical and/or physical modification, in one or more steps, of starch.

The term "oligipeptide" means a peptide composed of 2-10 aminoacids. So, the term "oligipeptide" encompasses bi-amino acids, i.e. a peptide composed of two amino acids. The oligopeptide is preferably a bi-amino acid, so that the term oligopeptide can in a specific embodiment be replaced by the term bi-amino acid.

Molecular weight measurements can be done by Gel Permeation Chromatography (GPC), particularly GPC-RI, or ion exchange chromatography or a combination of both. As far as glucans are concerned, GPC or GPC-RI are preferred. As far as amino acids or peptides are concerned, ion exchange chromatography is preferred. In order to obtain results for (average) molecular weights in a composition comprising glucans as well as glycerol, an amino acid, an oligopeptide, or a mixture of one or more thereof, molecular weight of glucans and the molecular weight of the other component can be determined singly and then the results be combined to obtain for example the average molecular weight for components a)-d) of the composition. So, in case of such composition, the method for determining Mw and Mn is preferably a combination of GPC or GPC-RI and ion exchange chromatography. If component a) is maltose, molecular weight can be determined in one sample, preferably with GPC or GPC-RI.

Molecular weight (M, unit g/Mol) may be calculated for any molecule or polymer. For example, the molecular weight of a glucan molecule is given by $$M \text{ (glucan molecule of } i \text{ units)} = 180 \text{ g/Mol} + (i-1) * 162 \text{ g/Mol},$$

wherein 180 g/Mol is the molecular weight of glucose and 162 g/Mol the molecular weight of each added glucose unit, after polymerization through hydrolysis.

No single number can adequately characterize the molecular weight of a preparation of saccharides. Therefore, various descriptors are used. The most commonly used are the "weight average molecular weight" (Mw) and the "number average molecular weight" (Mn):

$$Mw = \Sigma(n_i * M_i^2) / \Sigma(n_i * M_i)$$

$$Mn = \Sigma(n_i * M_i) / \Sigma(n_i)$$

where $n_i$ is the number of molecules of molecular weight $M_i$. Mw is particularly sensitive to changes in the high-molecular-weight content of the saccharide preparation whilst Mn is largely influenced by changes of the low molecular weight molecules in the sample.

The molecular weight of glycerol is 92 Dalton, or 92 g/Mol.

Amino-acids have molecular weight between 75 and 205 g/Mol.

Oligopeptides have the molecular weight of each of their composing amino-acids, in summary, subtracted by 18 g/Mol for each peptic bond, corresponding to the loss of 1 water molecule during peptic bond formation.

Average $M_w$ (Mw and Mn) of a mixture of amino acids and/or peptides may be calculated the same way as Mw for a mixture of saccharides.

$$Mw = \Sigma(n_i * M_i^2) / \Sigma(n_i * M_i)$$

$$Mn = \Sigma(n_i * M_i) / \Sigma(n_i)$$

The amount of individual amino-acids or oligopeptides within the mixture is either known or summed up.

Average Mw (Mw and Mn) of a mixture of Saccharides and non-saccharides, (e.g. can be calculated the same way than Mw of saccharides or amino-acids $$Mw = \Sigma(n_i * M_i^2) / \Sigma(n_i * M_i)$$

$$Mn = \Sigma(n_i * M_i) / \Sigma(n_i)$$

The amounts of all the different components of the mixture and their molecular weights are either known or summed up. Often, composition of an amino-acid mix is analyzed and communicated by the supplier, else they can be determined as stated hereunder.

Reliable techniques to analyze composition of amino-acids mixes or peptides imply ion exchange chromatography, with post column derivatization (e.g. with nin-hydrin Anders J C.

Advances in amino acid analysis. BioPharm Int. 2002; 4:32-39).

A "Poly-Dispersion Index" (Poly-D) of a sample may be calculated, as the ratio of Mw/Mn.

The degree of polymerization of a polymer molecule is defined as

DP=M (polymer molecule)/M (monomer) wherein in case of glucan M (monomer) is 162 g/mol.

So, every molecular weight (M) of glucan molecule can be expressed as DP and vice versa.

The terms DPw and DPn mean the weight average degree of polymerization and the number average degree of polymerization, and are defined as follows:

DPw=Mw/M (monomer)
DPn=Mn/M (monomer)

Molecular weights and degrees of polymerization, also average values thereof, are preferably measured by gel permeation chromatography (GPC), preferably by gel permeation chromatography with refractive index (RI) detection (GPC-RI). Ion exchange chromatography is also possible, particularly in case of peptides/amino acids. A specific method is further described in the examples.

The amount of a molecular fraction with a given molecular weight range can be indicated in many different ways. A very common and useful way to do so, is to express the amount of such fractions as weight percentages of the entire composition, no matter the final concentration at which such composition shall be applied in the final solution. In the present invention we express weight percentage of components a), b), c) or d) in percent of the total weight of a)+b)+c)+d). The total weight of a)+b)+c)+d) is also called "total CHO". Percentages related to the total weight of a)+b)+c)+d) are calculated on the basis of dry matter.

Weight percentages of glucan molecules, or fractions of glucan molecules, the fractions defined by DP or otherwise, within a glucose polymer preparation can be determined by GPC, particularly GPC-RI. Weight percentage of a glucan molecule or fraction can particularly be determined by determining the area for said glucan molecule/fraction in a GPC chromatogram and determining its relation to the area of the species, e.g. all glucan molecules, to which it shall be set in relation. Knowing the area of all glucans within the composition of the invention then allows to calculate weight percentages of glucan molecules, or fractions of glucan molecules, within a)-d) (wherein a)-d) are as defined above). For example:

wt-% of fraction or molecule or interest=[(area of molecule or fraction of interest)/(area of total CHO)]*100 wherein the area means the area in the GPC-chromatogram.

The detailed procedure of determination of percentages of molecules or fractions is known to skilled persons in this field and it is not necessary to limit the method on details. As known, in GPC, the concentration by weight of polymer in the eluting solvent may be monitored with a detector. The molecular weight can be determined with molecular weight standards. The examples describe measures, that may be combined with the above procedure: total amount or concentration of a glucose polymer preparation may correspond to the area under the curve of a GPC chromatogram after background-substraction, followed by a calibration using molecular weight standards, particularly Icodextrin, maltose and glucose standards. Quantification of molecular weight fractions or molecules may be assessed by using molecular weight standards, such as dextran molecular weight standards and Icodextrin as a comparative standard.

In a liquid composition, the weight percent of components may alternatively be defined on basis of the whole mass of the whole liquid composition.

In this invention the term "Physiological Concentrations of Salts" is used to describe the following concentrations:

sodium at a concentration from about 100 to about 150 mEq/L;

potassium at a concentration from about 0 to about 10 mEq/L;

calcium at a concentration from about 0 to about 10 mEq/L;

magnesium at a concentration from about 0 to about 10 mEq/L;

The term "peritoneal therapeutic fluid" (PTF), as used in the present application, refers to an aqueous solution comprising physiological amounts of various electrolytes in concentrations comparable to those found in blood. Common peritoneal dialysis fluids may comprise:

sodium at a concentration from about 100 to about 150 mEq/L;

potassium at a concentration from about 0 to about 10 mEq/L;

calcium at a concentration from about 0 to about 10 mEq/L;

magnesium at a concentration from about 0 to about 10 mEq/L;

an "Osmotic Agent", such as glucose and/or maltodextrin or other mono- and/or polymeric saccharide molecules, amino-acids and peptides, cyclodextrins, polyethelyne glycols (PEGs), glycerol, dextranes, and other biocompatible compounds at concentrations high enough to generate osmotic pressure, derivatives of such compounds and mixtures of such compounds and/or their derivatives, with the Osmotic Agent being at a final combined concentration between 0.5 and 20%.

A PTF may be applied into the peritoneum in order to fulfill treatment of the peritoneum itself or systemic treatments. Examples for treatment of the peritoneum are chemotherapies against peritoneal cancer, or against peritoneal infections. A very common example for systemic treatment by peritoneal fluids is peritoneal dialysis, where low molecular waste products are eliminated from the blood circulation, in most cases because of renal malfunction.

A "peritoneal dialysis fluid" (PDF) is a liquid mixture to be introduced and maintained in the peritoneal cavity of a patient in need of dialysis, to cleanse the blood and balance its constituents, for a time period of for example 1 to 16 hours, sufficient to remove blood waste products and water from the patient. At the end of said period, a "dialysate" is removed from the patient's peritoneal cavity.

Peritoneal dialysis dwell times vary from less than 2 hours, for example in automated peritoneal dialysis (ADP); over 4 to 6 hours, for example in continuous ambulatory peritoneal dialysis (CAPD); to 8 to 12 hours in long dialysis dwells, for example whole day or whole night dwells.

In this application, dwells of up to 6 hours are referred to as short PD dwells, whereas dwells of 8 hours and longer are referred to as long dwells.

The term "ultra-filtration" (UF) describes exchange of fluids and dissolved substances (e.g. fluid, electrolytes, urea, creatinin, glucose, and other small molecules) per unit of time. Ultra-filtration during dialysis occurs from the blood compartment into the peritoneal compartment, containing the dialysate. On the other hand, solutes and liquid from the dialysate may back transfer into the patient's system, either by lymphatic absorption, or by back-ultra-filtration, of small molecules or liquid from the dialysate into the blood.

In the context of the present invention, the term transcapilary ultrafiltration corresponds to all body fluids that transfers from the body into the dialysis fluid, during the peritoneal dialysis dwell.

The term net-ultrafiltration (NUF), is established subtracting the recovered dialysate Volume (RDV) at the end of the dialysis dwell, from the volume of initially administered PD Fluid (IPFV):

NUF=RDV−IPFV

NUF is the result of transcapillary ultrafiltration (TCUF) (out of the blood into the dialysis fluid) versus lymphatic absorption (LA) of dialysis fluid (out of the peritoneal cavity into the body):

NUF=TCUF−LA.

Net ultra-filtration may be positive (fluid elimination from the patient into the dialysate), which corresponds to one of the aims of dialysis or negative (overall fluid uptake from the peritoneum into the patient), e.g. when the osmotic pressure was not sufficiently sustained over the time of the dialysis dwell.

Lymphatic absorption (LA) can be assessed based on the initially administered PD Fluid Vol(PDF)$_i$ multiplied by the quantitative loss of an intra-peritoneally administered volume marker such as dextran 70:

$$LA(ml) = \frac{(Dx_i - Dx_t)}{(Dx_i)} * Vol(PDF)i$$

Transcapilary Ultra-filtration (TCUF) can then be calculated by addition of Lymphatic absorption and net-ultrafiltration:

TCUF=NUF+LA.

The term "total CHO" is applied to the total amount of carbohydrates present in a PTF.

The term "CHO absorption" is applied to describe the total "amount of carbohydrates" (CHO) absorbed by the patient from the PDF in the peritoneum, during a peritoneal dialysis (PD) dwell. Carbohydrate absorption is assessed as means of metabolizable osmotic agent absorbed by the body during a dialysis dwell. It is established by subtracting total carbohydrate amount of recovered dialysate from total carbohydrate amount of initially administered PD fluid.

Glycerol, which is a carbohydrate derivative, is also regarded as a carbohydrate, and, if applied, is accounted within the terms "total CHO" and "CHO— absorption".

Strictly speaking, amino-acids and peptides are not carbohydrates, since they also contain Nitrogen atoms. But since the interest of total CHO and CHO absorption is mainly to estimate metabolizable components within the PTF, and in order of simplicity, we will account for amino-acids and oligopeptides within the terms "total CHO" and "CHO absorption".

The term "Rate of NUF per CHO absorption" is applied to describe the ratio of the NUF Volume (ml) over the total weight of CHO absorption (mg), during a dialysis dwell.

"Near to physiological blood pH" corresponds to a pH of 6.5 to 8, preferably of 6.8 to 7.7, more preferably of 7 to 7.5.

Hereinafter, molecular weight ranges are described. Each of the ranges comprises one or more chain lengths of glucan molecules, expressed in DP. The ranges are intended to facilitate a comparison with prior art, wherein such ranges are indicated. Moreover, these ranges are used to define specific embodiments of the invention, as described in the detailed description. Please note that the boundaries of these ranges are rounded values. Since it has been used in many publications and patents as such, we integrate DP information in our analyses of anterior publications and patents on glucose polymers in the following manner.

| DP | molecular weight(D) | molecular weight range(D) |
|---|---|---|
| 1 | 180 | <200 |
| 2 | 342 | 200-400 |
| 3 | 504 | 400-600 |
| 4 | 667 | 600-750 |
| 5 | 829 | 750-900 |
| 6 | 991 | 900-1000 |
| 7 | 1153 | 1000-1250 |
| 8 | 1315 | 1250-1400 |
| 9 | 1477 | 1400-1500 |
| 10 | 1639 | 1500-1750 |
| 11 | 1802 | 1750-1900 |
| 12 | 1964 | 1900-2000 |
| 13 | 2126 | 2000-2250 |
| 14 | 2288 | 2250-2400 |
| 15 | 2450 | 2400-2500 |
| 16 | 2612 | 2500-2750 |
| 17 | 2774 | 2750-2800 |
| 18 | 2937 | 2800-3000 |
| 19 | 3099 | 3000-3250 |
| 20 | 3261 | 3250-3300 |
| 21 | 3423 | 3300-3500 |
| 22-24 | | 3500-4000 |
| 25-27 | | 4000-4500 |
| 28-30 | | 4500-5000 |
| 31-33 | | 5000-5500 |
| 34-36 | | 5500-6000 |
| 37-39 | | 6000-6500 |
| 40-43 | | 6500-7000 |
| 44-46 | | 7000-7500 |
| 47-49 | | 7500-8000 |
| 50-55 | | 8000-9000 |
| 56-61 | | 9000-10000 |
| 62-67 | | 10K-11K |
| 68-73 | | 11K-12K |
| 74-76 | | 12K-12.5K |
| 77-80 | | 12.5K-13K |
| 81-86 | | 13K-14K |
| 87-92 | | 14K-15K |
| 93-98 | | 15-16K |
| 99-104 | | 16K-17K |
| 105-110 | | 17K-18K |
| 111-117 | | 18K-19K |
| 118-123 | | 19K-20K |
| 124-129 | | 20-21K |

DETAILED DESCRIPTION OF THE INVENTION

Embodiments described in this detailed description can be combined in any combination sub-combination in this invention.

The composition may be abi-modal composition, which means that in the molecular weight distribution two peaks are present, one peak in a smaller molecular weight region and one and a higher molecular weight region. In this aspect, the composition may comprise a glucan (preferably an alpha-glucan) polymer preparation, preferentially a maltodextrin or a maltodextrin derivative, and as further components may comprise one or several of: maltose, glucose, glycerol, amino-acid, and/or oligopeptide, which may be added to the polymer preparation. For example, in peritoneal dialysis, abi-modal osmotic agent maybe a maltodextrin preparation (for example Icodextrin), to which maltose, glucose, glycerol, amino-acid, and/or oligopeptide, is added.

Even if the singular term "amino acid" or "peptide is used herein, the plural, particularly a mixture of these, is encompassed.

The term "polymer" is intended to encompass also "oligomers".

A preferred glucan is dextrin, dextran and/or derivatives of such. A preferred dextrin is maltodextrin.

The composition may be a solid composition. The composition may be a dry composition. The composition may be obtained by drying a liquid aqueous composition which can be obtained by a method of the invention as described hereinafter.

The composition of the invention may comprise further ingredients, such as one or more of: salts, other compounds than defined in a)-d), trace elements, enzymes, other osmotic agents, and/or active pharmaceutical ingredients. Preferably, components a)-d) is at least 90 wt-% of the total composition, even more preferably at least 95 wt-%, more preferably at least 98 wt-%.

In a further related aspect claimed compositions may be mixed with other osmotic agents.

The glucan molecules of DP>10. DP>24, DP>55, or still further glucan molecules mentioned below with higher DP, are part or fractions of component d) which are the glucan molecules with DP>4.

If ranges of components b) (glucose) or c) (glucan molecules of DP 3 and DP 4) are indicated with the expression "less than", a lower limit of such range is more than 0 wt-%, preferably at least 0.01 wt-% of the total weight of a)-d), more preferably at least 0.1 wt-% of the total weight of a)-d). So, components b) and c) are always present.

If ranges of other components are indicated with the expression "less than", a lower limit of such range is preferably more than 0 wt-%, more preferably at least 0.01 wt-% of the total weight of a)-d), even more preferably at least 0.1 wt-% of the total weight of a)-d).

Mw of the composition is Mw 0.8-15 kD, preferably Mw 1-10 kD, more preferably 1.2-6.2 kD or 1.0-6.2 kD, more preferably the range of 1.4-6 kD, more preferably 1.6 to 5.8 kD. Other possible ranges are 1.3-6 kD, 1.5-5.8 kD, 1.5 to 5 kD.

These ranges of Mw can be combined with any ranges of Mn. Mn of the composition is preferably 0.2-3 kD, preferably the range of 0.3 to 3 KD, more preferably 0.5 to 3 KD or 0.7-3 kD, more preferably 0.8-2.7 kD, more preferably 0.9-2.6 kD. Other ranges are 1-2.7 kD, 1.2-2.5 kD.

In one embodiment of the composition, glucan molecules of DP>111 are present in an amount of less than 1.5 wt-% of the total weight of a)-d).

In one embodiment of the composition, glucan molecules of DP>246 are present in an amount of less than 0.6 wt-% of the total weight of a)-d).

In one embodiment, the composition comprises the glucose in a content of less than ⅓ the content of ingredient a) of the composition (a compound that is selected from the group consisting of maltose, glycerol, an amino acid, an oligopeptide, or a mixture of one or more thereof), specifically less than ⅓ the content of maltose, if maltose is used as ingredient a).

In one embodiment, the composition comprises the glucan molecules of DP 3 and DP 4, taken together, in a content of less than ⅓ of the content of ingredient a) of the composition (a compound that is selected from the group consisting of maltose, glycerol, an amino acid, an oligopeptide, or a mixture of one or more thereof), specifically less than ⅓ the content of maltose, if maltose is used as ingredient a).

In one embodiment, the composition comprises ingredient a) of the composition (a compound that is selected from the group consisting of maltose, glycerol, an amino acid, an oligopeptide, or a mixture of one or more thereof), particularly maltose, in a content of 8 to 65 wt-% of the total weight of a)-d).

In one embodiment, the composition comprises the glucan molecules of DP>4 in a content of more than 16 wt-%, preferably more than 21 wt-% of the total weight of a)-d).

In one embodiment, the content of glucan molecules of DP 3 and DP 4, taken together, is less than 15 wt-% of the total weight of a)-d), more preferably less than 10 wt-% of the total weight of a)-d), even more preferably less than 5 wt-% of the total weight of a)-d).

In one embodiment, the content of glucan molecules of molecular weight of 0.8 to 1.5 kD, or DP5-DP9, is 4-39 wt-%, preferably 6-23 wt-%, of total CHO.

In one embodiment, the content of glucan molecules of molecular weight of 1.5 to 4.5 kD, or DP10-DP27, is 16-60 wt-%, preferably 20-60 wt-%, of total CHO.

In one embodiment, the content of glucan molecules of molecular weight of 4.5 to 9 kD, or DP28-DP55 is less than 48 wt-%, preferably less than 45 wt-%, of total CHO.

In one embodiment, the content of glucan molecules of molecular weight smaller than 9 kD, or DP<55, is more than 85 wt-% of total CHO, more preferably more than 90 wt-% of total CHO.

In one embodiment, the content of glucan molecules of molecular weight of 0.8-4.5 kD, or DP5-DP27, is more than 18 wt-%, preferably more than 25 wt-%, even more preferably more than 30 wt-%, of total CHO.

In one embodiment, the content of glucan molecules of DP 3 and 4 is less than 30 wt-%, preferably 2 to 26 wt-%, more preferably 2 to 15 wt-%, even more preferably 2 to 10 wt-%, of total CHO.

In one embodiment, the content of glucan molecules of DP 5 and 6 is less than 35 wt-%, preferably 1 to 15 wt-%, of total CHO.

In one embodiment, the content of glucan molecules of DP 7 to 10 is less than 35 wt-%, pref 1 to 18 wt-%, of total CHO.

In one embodiment, the content of glucan molecules of DP<10 is 15-85 wt-%, preferably 20-80 wt-%, of total CHO.

In one embodiment, the content of glucan molecules of DP>25 is 1.9-59.5 wt-%, preferably 3.9-57.5 wt.-%, preferably 4.9-55.8 wt-% of total CHO.

In one embodiment, the content of glucan molecules of DP>30 is less than 59 wt-%, preferably less than 55 wt-%, more preferably less than 50 wt-% of total CHO.

In one embodiment, the content of glucan molecules of DP>111 is less than 1.5 wt-% of total CHO.

In one embodiment, the content of glucan molecules of DP>246 is less than 0.6 wt-% of total CHO.

As mentioned before, features of this specification can be combined in any manner and any number. In a very specific embodiment, which reflects only one possible combination, the present invention provides with a composition, comprising:
- a) a compound that is selected from the group consisting of maltose, glycerol, an amino acid, an oligopeptide, or a mixture of one or more thereof, preferably maltose, in a content of 5 to 75 wt-% of the total weight of a)-d), preferably 8-65 wt-%, even more preferably 10-55 wt-%,
- b) glucose in a content of less than ½, pref less than ⅓, of the content of a), and in a total content of less than 5 wt-% of the total weight of a)-d),
- c) glucan molecules of DP 3 and DP 4, taken together, in a content of less than ½, preferably of less than ⅓, of the content of a),
- d) glucan molecules of DP>4 in a content to give 100 wt-% together with a), b) and c), wherein
  - glucan molecules of DP 3 and 4 are present in an amount of less than 30 wt-%, preferably 2 to 26% wt-%, of the total weight of a)-d),
  - glucan molecules of DP 5 and 6 are present in an amount of less than 35 wt-%, preferably 1 to 15 wt-%, of the total weight of a)-d),
  - glucan molecules of DP 7 to 10 are present in an amount of less than 35 wt-%, preferably 1 to 18 wt-%, of the total weight of a)-d),
  - glucan molecule of DP<10 are present in an amount of 15-85 wt-%, preferably 20-80 wt-%, of the total weight of a)-d),
  - glucan molecules of DP>10 are present in an amount of 15-85 wt-%, preferably 20-80 wt-%, further preferably 35-80 wt-%, of the total weight of a)-d),
  - glucan molecules of DP>24 are present in an amount of 2-60 wt-%, preferably 4-58 wt-%, preferably 5-56 wt-% of the total weight of a)-d),
  - glucan molecules of DP>25 are present in an amount of 1.9-59.5 wt-%, preferably 3.9-57.5 wt.-%, preferably 4.9-55.8 wt-% of the total weight of a)-d),
  - glucan molecules of DP>30 are present in an amount of less than 59 wt-%, preferably less than 55 wt-%, more preferably less than 50 wt-% of the total weight of a)-d),
  - glucan molecules of DP>55 are present in an amount of less than 15 wt-%, preferably less than 12 wt-%, more preferably less than 10 wt-%, still more preferably less than 8 wt-% of the total weight of a)-d),
  - glucan molecules of DP>111 are present in an amount of less than 1.5 wt-% of the total weight of a)-d),
  - glucan molecules of DP>246 are present in an amount of less than 0.6 wt-% of the total weight of a)-d), The weight average molecular weight of a)-d), taken together, may be Mw 0.8-15 kD, preferably Mw 1.0-10 kD, more preferably Mw 1.2-6.2 kD or 1.0-6.2 kD, more preferably 1.4-6 kD, more preferably 1.6 to 5.8 kD, The number average molecular weight of a)-d), taken together, may be Mn 0.2-3 kD, preferably Mn 0.3-3 kD, more preferably Mn 0.5-3 kD or 0.7-3 kD, more preferably 0.8-2.7 kD, even more preferably 0.9-2.6 kD. Ranges of Mw and Mn can be combined in any manner.

Hereinafter, embodiments concerning branching are described.

When %-values of branching are indicated, these values mean mol-%. The degree of branching is defined herein as the percentage number of glucose monomers comprising a branch (i.e. incorporated by three bonds within a glucan molecule) based on the total number of all glucose monomers measured in a sample of the glucan of the invention with randomly distributed molecular weights.

The degree of branching is measured by the method of standard methylation analysis or alternatively by the method of reductive degradation after methylation. These methods may be performed as described described in patent application WO 2007128559 A2, but in the present invention with glucans instead of fructans which were measured in WO 2007128559 A2.

In one embodiment of this invention branching of the glucan starting material or final preparation may be altered by parameters including the choice of the starting material, by use of branching enzymes, and/or by incubation at chosen physico-chemical conditions during, favoring aimed branching of the end-product.

Preferable physicochemical conditions include incubation at acidic or basic pH, a temperature between 20 to 150° C., at pressures up to 10 bars, for variable times (between 1 minute and 100 hours, before, during, or after enzymatic treatment.

Branching enzyme include for example amylases, amyloguosidases, and transglucosidases.

Polyglucose chains in starch or dextrins are majorly formed by alpha 1,4 bounds. Branching of starch or branching of of dextrins is defined of the percentage of alpha 1,6 bounds.

Dextran contains polyglucose chains majorly formed by alpha 1,6 bounds. Branching of dextran is defined as the percentage of alpha 1,3 bonds.

In the frame of this invention, the term of branching shall be enlarged to any multiple nature of bonds within a glucan preparation.

The invention in particular relates to above preparations of soluble saccharide polymers, which can be part of the composition of the invention, where saccharide polymers are dextrins or dextrin derivatives, and preferably where dextrin branching by 1,6 glycosidic bonds is higher than 11%, preferably higher than 12%, even more preferably higher than 13%, still more preferably higher than 15%, or higher than 17.5% or higher than 20%

The invention in particular relates to above preparations of soluble saccharide polymers, which can be part of the composition of the invention, where saccharide polymers are dextrins, where branching by 1,6 glycosidic bonds is lower than 7%, preferably lower than 6%, even more preferably lower than 5%, still more preferably lower than 4%, or lower than 3%, or lower than 2%, or lower than 1%, or lower than 0.1%.

The option of low or high branching to saccharide polymer compositions may be intended for the following aim: Highly branched glucans degrade more slowly under the activity of amylases, and therefore will degrade more slowly during peritoneal dialysis. Depending on residual renal function of patients, one could adapt the polymer stability.

Less branched or unbranched unbranched saccharide polymers, for example in concentrated (e.g. 3 to 6%) solutions, could be applied to patients with high residual renal function. Increased degradation by degrading enzymes would increase possible uptake of small molecular weight degradation products, keep ultrafiltration low and even allow some back diffusion of liquid from the dialysate into the patients system. Small molecular weight compounds such as maltose, iso-maltose, or the like would be excreted by the kidneys before being transformed to glucose by intra-cellular maltases. As a result, sufficient ultra-filtration would occur to guaranty low molecular weight products to enter the dialysate, but an overall low ultra-filtration would sustain remaining residual renal function.

Low alpha 1-6 branching would further be advantageous for patients suspected for wheat allergies.

Higher concentrated solutions (e.g. 5 to 7.5%), for example with highly branched maltodextrins, could be applied to patients with low or no further residual renal function, to increase UF rate and NUF, and to reduce enzymatic degradation, maintaining hyper-osmolality for a longer time and reducing CHO uptake by the patient during the dialysis dwell.

In one embodiment of the composition the glucan or glucan molecules are derivatized. A definition of "derivatized" was given earlier.

Derivatization may be done by enzymatic, chemical and/or physical modification.

Glucan may be modified by etherification, esterification, alkylation, crosslinking, oxidation, reduction, treatment with alkali and/or hydrolysis, particularly acidic or enzymatic hydrolysis.

Particularly one or more OH groups in the glucan may be modified in this way.

In a specific embodiment "derivatized" means that one or several OH groups in the glucan are modified. The modification is particularly a substitution or functionalization of one or several OH groups of the glucan. The modification may be a modification at one or more terminal OH groups, OH groups at reducing ends and/or other OH groups.

The derivative may be a sugar-alcohol, particularly glucitol, a sugar-acid, particularly gluconic acid, or an alkylglycoside.

In a specific embodiment, one or more OH groups may be modified to a group —O—R, wherein R is selected from the group consisting of
  i) a substituted or unsubstituted, branched or linear, saturated or unsaturated hydrocarbyl group, particularly alkyl or hydroxyl alkyl, particularly selected from methyl ethyl, propyl (n- or iso), butyl (n, iso or tert), hydroxyethyl, hydroxypropyl (n- or iso), hydroxybutyl (n, iso or tert), $CH(CH_2OH)_2$, $CH(CH_2(OH))_2$, $CH(CH_2OH)(CHOHCH_2OH)$. This modification is particularly applicable to a terminal or a reducing OH group, optionally also to other OH groups,
  ii) OH, —O-saccharide, -hydrocarbyloxy, substituted -hydrocarbyloxy, and -sulfoxy, CO—NH—(CH2)n-COOH, —CO—NH—(CH2)n COO—, —CN, —Cl, —Br, —I, —$NO_2$, —(CH2)CN, —(CH2)n-Cl, —(CH2)n-Br, —(CH2)n-I, —(CH2)n-$NO_2$, —O—$PO_3^{2-}$, —O—$PO_3H$—, —O—$PO_3H_2$, —$NH_2$, —NH-alkyl, —N(-alkyl1,-alkyl2), —$N^+H_3$, —$N^+H_2$-alkyl, —$N^+H$(-alkyl1,-alkyl2), —$N^+$(-alkyl1,-alkyl2,-alkyl3), —$B(OH)_2$, —CHO, —CO-alkyl), —$CF_3$, —CN, —CH2CN, wherein alkyl may be a linear or branched (C1-C5) alkyl, a partially unsaturated alkyl.

In another embodiment the present invention provides a solution of glucan starting material or intermediate or final preparation in water, providing a solution of NaOCl, and adding the NaOCl solution to the starch solution to oxidate the starch. Such oxidation may be leading to transformation of the glucane to a gluconic acid.

Another embodiment the invention provides dissolving of glucan starting material or intermediate or final preparation in an acid and an alcohol. Such dissolution may occur for 1 to 40 hours. Such dissolution may be heated up to 100°, eventually up to higher temperature up to 150° C. under pressure. Such mixture under such conditions, may hydrolyze the starch and alkylate it.

In another embodiment glucan starting material or intermediate or final preparation may be submitted to ether synthesis, using alkylene-oxides such as methylene-, ethylene-, propylene-, butylenes_oxide.

"Intermediate preparation" is particularly intended to mean a preparation of components b)-d) of the composition, before a) is added, particularly when a) is not maltose.

The glucan in the invention may be free or substantially free of terminal formaldehyde, aldonic acids, and/or furfurals.

In a further aspect, the present invention provides with a liquid aqueous composition, comprising the composition of the invention and water. This liquid composition may be a solution, a dispersion, an emulsion or a mixture of a solution, dispersion and/or or emulsion, or a mixture of solution and dispersion, preferably a solution which means that the composition, and other constituents, if present, is/are dissolved in the liquid phase. The liquid phase and liquid composition may be predominantly (more than 90 vol-%, preferably more than 95 vol-% of the liquid phase), or solely, water.

The liquid aqueous composition may be a dialysis fluid or used as a dialysis fluid, particularly for peritoneal dialysis.

The liquid aqueous composition may have a ph of 6.8 to 7.7.

The liquid aqueous composition, particularly if it is a solution for dialysis, may also comprise buffering agents (lactate, acetate, gluconate in particular) and other additives such as aminoacids, insulin, polyols such as, for example, sorbitol, erythritol, mannitol, maltitol or xylitol, or hydrogenated starch hydrolysates.

In one embodiment, the liquid aqueous composition has an osmolality of 280 to 450 mosm/kg, preferred 290 to 420 mosm/kg.

In a further aspect of the invention, the composition as described above, or the liquid aqueous composition as described above is intended for use as a medicament or medication or for use in therapy.

More specifically, the composition as described above, or the composition as described above, or the liquid aqueous composition as described above is intended for use as
  peritoneal therapeutic fluid or solution, particularly with reduced cytotoxicity
  dialysis fluid or solution, particularly peritoneal dialysis fluid or solution, particularly with reduced cytotoxicity
  gastroenterological solution, such as digestive tract cleaning solutions,
  nutritional solution
  nutritional infusion,
  drug administration solution
  detoxifying solution
  physiological substitute or additive preparation, particularly for physiological body fluids, more particularly as substitute or addition for blood, plasma, serum, or interstitial body fluids
  adhesion reducing solution after surgery,
  solution for clyster,
  laxative,
  osmotic agent, particularly osmotic driver
  infant dietetic
  pharmaceutical agent with reduced cytotoxicity,
or in treatment of renal diseases.

The composition as described above, or the liquid aqueous composition as described above may have a reduced cytotoxicity in comparison with products known so far. So, it may be used for its own, or in one or more of mentioned applications, as agent with reduced cytotoxicity.

Preferred medical solutions are solutions to replace or add to physiological body fluids, such as blood, serum, and interstitial body fluids or solutions for gastroenterological application, such as digestive tract cleaning solutions, clistiers, and nutritional solution. Solutions for intravenous, intraperitoneal, or other subcutaneous applications are also included. Preferred medical solutions are peritoneal therapeutical solutions. Preferred peritoneal therapeutical solutions are peritoneal dialysis solutions.

In the context of a medical application the solution may be applied to the human body, where control of osmolality plays a role, either because physiological osmolality is intended or because hypo- or hyper-osmolality is the aim.

A preferred medical application is the use of a composition of the invention, particularly a bimodal composition, as an osmotic agent to adapt the medical solution to its specific aim. Different medical solutions may have different osmotic pressures, for example for blood substitutions the osmotic pressure of the medical solution may be near to physiological concentration, whereas hyper-osmotic pressure may be applied for intestinal or peritoneal applications.

In a further aspect, the composition of the invention is applied as osmotic agent to PTFs or PDFs. In a further related aspect, a PTF, containing a claimed composition as osmotic agent, is characterized by the application of a combination of two or more different of compositions of the invention.

As to the use as osmotic driver, particularly in a PDF, mentioned compositions can be used to generate a significantly higher NUF fluid volume than Icodextrin 7.5%, with a comparable or higher Rate of NUF per CHO absorption, when applied as sole osmotic agent, at concentrations less than 7.5%, preferably less than 7.2%, within a buffered solution of physiological salt concentrations, for example in dwells of 2, 4 or 6 hours in peritoneal dialysis.

As stated above, compositions of the invention find use in different fields, including the following:
in infant dietetics, and feeding of medical patients;
in the make-up of blood plasma substitutes;
in the preparation of enteral and parenteral treatments;
in the manufacturing of PTFs;
and in the manufacture of dialysis solutions for the treatment of renal diseases.

The term "composition for medical application", comprises any kind of physiologically applicable solutions, such as gastroenterological solution, which may be drinkable, nutrient infusions and other drinkable applications, drug administration and detoxifying solutions, physiological substitute preparations, or adhesion reducing solutions after surgery. A preferred application of compositions for medical application in this invention are peritoneal therapeutic fluids (PDF) or peritoneal dialysis fluids (PTF).

In a further aspect, the present invention provides a composition described hereinabove, applied to the manufacturing of dialysis solutions.

In a further aspect, the present invention provides a peritoneal dialysis fluid comprising a composition according to the invention.

In a further aspect, the invention provides a pharmaceutical composition including a PTF as defined above.

In a further aspect, the present invention provides the use of described compositions to generate a higher UF or NUF fluid volume than Extraneal® (icodextrin 7.5%), with a comparable or higher rate of NUF (Volume) per CHO (weight) absorption, when applied as sole osmolar agent at concentrations of less than 7.5%, within a buffered solution of physiological salt concentrations, in peritoneal dialysis dwells of 6 hours or less.

Hereinafter, methods for obtaining products of the invention are described.

The glucan polymers in a composition of the present invention, particularly components b)-d) (preferably in combination), or the composition if component a) is maltose, may be prepared by acid and/or enzymatic hydrolysis of industrial saccharide solutions; enzymatic repolymerisation and branching; followed by fractionation. Or they may be prepared by ongoing fractionation, during such reactions, continuously separating reaction products out of the mixture. Different intermediate preparations may be carded out separately and mixed together later. Other low molecular weight molecules, such as a compound that is selected from the group consisting of maltose, glycerol, an amino acid, an oligopeptide, or a mixture of one or more thereof, may be added later, to obtain the aimed final composition. Industrial saccharide solutions include starch syrups and maltose syrups. Industrial saccharides may be pretreated for substitutions, partial substitutions or branching of their saccharide content, or intermediate polysaccharide preparations may be treated to this aim.

In still a further aspect, the invention is directed to a method for producing a liquid aqueous composition as described above, comprising
preparing an aqueous solution of starch, having a solids content of from 10 wt-% to 80 wt-%;
gelatinization, by treating said solution successively with a specific combination of enzymes chosen from amyloglucosidase and/or amylase,
purifying the solution,
fractionating the solution in such a way as to eliminate or decrease molecular-weight saccharide fractions having a molecular weight higher than 40000 D, and to recovering the other fractions,
adding a compound that is selected from the group consisting of maltose, glycerol, an amino acid, an oligopeptide, or a mixture of one or more thereof, preferably maltose.

By fractionation and addition of a compound that is selected from the group consisting of maltose, glycerol, an amino acid, an oligopeptide, or a mixture of one or more thereof, maltose and/or glucose, a composition as defined above is obtained in the solution.

In a further step, glucose may be added. Glucose may be added separately or together with a compound that is selected from the group consisting of maltose, glycerol, an amino acid, an oligopeptide, or a mixture of one or more thereof. For example, when adding maltose, a maltose product a can be added that comprises glucose. Maltose often comprises quantities of glucose, for example when maltose syrup is added.

A dry composition of the invention can be obtained by drying the product of the aforementioned process.

The initial ratio of amylase/amylopectin of specific starches maybe exploited to simplify generation of high or low branched maltodextrins, as required for specific applications.

Preferred soluble glucose polymers in the present invention are dextrins produced by enzymatic treatment of starch.

Such soluble glucose polymers of the present invention are particularly prepared according to a process comprising the combination of several or all of the following steps:

1) choosing a starch of a defined amyopectin content, depending on the degree of branching aimed for the maltodextrin or saccharide polymer preparation;
2) choosing or preparing an aqueous solution of starch, having a solids content of from 10% to 80% by weight;
3) optionally treating said solutions with a branching enzyme, if a defined branching is aimed
4) optionally derivatizing,
5) gelatinization, by treating said solution successively with a combination of enzymes chosen from amyloglucosidase or amylase (e.g. 0.1% thermophilic amylase at pH 6 at 80 to 98° C.), preferably for between 5 and 10 minutes;
6) optionally fractionating several solutions (e.g. one for high molecular weight of 4500 to 9000 D, one of molecular weight of 1500 to 18000 D and one for low molecular weight of 200 to 1500 D), to be further mixed, such a step allowing high flexibility, a large spectrum of molecular weights of polymers in the final preparation, and at the same time, highest stringency of selected polymers in the final medical application.
7) purifying the solution, for example by treatment on activated carbon, or by filtration (e.g. glass pore filter, ceramic filters, or filter membranes), or by affinity procedures;
8) fractionating the solution in such a way as to eliminate or highly decrease high-molecular-weight saccharide fractions, preferably those having a molecular weight higher than 40000 daltons, further preferably higher than 18 kD and to recover the other fractions;
9) choosing or preparing a maltose enriched powder or solution;
10) optionally adapting low-molecular-weight fractions, preferably of 200 to 1500 D, to NUF needs of the solution by addition of maltose, and optionally adding glucose, for example up to 0.2% w/v/glucose total concentration of the final solution.

Above mentioned steps can also be used to further define steps that were mentioned previously in a more general method.

When the solution is obtained by dissolving the polymers according to the invention in water, it should be clear and colorless. It is preferably free of endotoxins, of peptidoglycans and of beta-glucans, and also of contaminants originating from the starting material or from the enzymatic preparations used to produce it.

To this effect, any highly branched polymers used in said solution will preferably have undergone purification so as to remove any coloration or any unwanted contaminant such as proteins, bacteria, bacterial toxins, viruses, fibers, traces of metals, etc. This purification step can be carried out according to the techniques known to those skilled in the art.

One step of the process in accordance with the invention may consist in collecting the fractions of suitable molecular weight to generate sought glucose polymer preparation. These fractions can be combined as they are, the polymers can be precipitated by adding ethanol, purified and dried under vacuum or else by spray drying, or any technique known to those skilled in the art.

In a further aspect the invention is directed to a container, for example PDF container, or kit comprising at least one compartment, containing a liquid aqueous composition as described above, for example as an osmotic agent, or a dry composition as described above. A container or kit according to the invention may have a second compartment containing a further part of the dialysis fluid, which, upon mixture with the acidic fluid from the first compartment, reconstitutes a dialysis fluid with a pH between 7.0 and 7.5. Another compartment of the container may comprise a buffer solution. The liquid aqueous composition in the first compartment may have acidic pH, like to 1-6 or 2-4. The buffer solution may have a pH suitable to produce the resulting pH the range of pH 6.5 to 8, preferably of 6.8 to 7.7, more preferably of 7 to 7.5.

EXAMPLES

In these Examples, the term "Extraneal" means a registered trade mark.

Example 1: Industrial Saccharide Polymer Preparation

A starch milk is prepared from an acid-fluidified, commercially available corn starch. A suspension of starch containing 20 to 50% solids is prepared by stirring, until complete solubilization at 90° C. The solution is then cooled to 60° C. and adjusted to pH between 6 and 6.5, by citric acid.

For gelatinization, a treatment with 0.1% heat-stable alpha-amylase of the starch is carried out in the reaction medium, and the reaction is stopped by heating between 88 to 92° C. for 5 to 10 minutes.

For dextrinization the pH is adjusted to 4 to 5, the concentration of amylase is increased to 0.3% and the reaction is carried out for several further hours. Dextrinisation may happen The final solution is fractionated in several steps on, including 30,000 10,000 5,000 dalton fractionation devices such as membrane or ceramic filters.

Table I shows two target glucan intermediate preparations or compositions of the physicochemical characteristics of two PDF solutions in presence of physiological salt conditions and pH 6.8 to 7.5, in accordance with the invention thus obtained.

TABLE I

| Intermediate scale PDF fluid production | | |
|---|---|---|
| PDF | Sol. 1 | Sol. 2 |
| [CHO] (w/v) | 5.0% | 6.8% |
| total weight (g) in 2 L | 100 | 136 |
| Osmolality (mOsm/kg) | 290 to 350 | 320 to 340 |
| Number average Mn (kD) | 1.1 to 1.5 | 1.4 to 2.0 |
| Weight average Mw (kD) | 2.1 to 3.5 | 3.5 to 6.0 |
| Poly-D | 1.5 to 2.0 | 2.2 to 2.8 |
| Osmolality (mOsm/kg) | 300 to 320 | 320 to 340 |

Example 2: Experimental Preparation

In this example we generated polysaccharide preparations and final osmotically active compositions of Mw between 3.4 and 6.1 kD and Mn between 2 and 3.7 kD.

In all cases such polymer fractions contained less than 1.5 wt-% of polymers with a higher molecular weight than 18 kD, and even less than 0.6 wt-% of polymers with a molecular weight higher than 40 kD.

Starting material was Icodexrin from commercially available Extraneal®. Batches of 80 Liters were submitted to 0.5 $m^2$ pelicon 2 Ultracel® membranes as recommended by the supplier, at 3 to 4 L/m2 at entrance pressure of less than 2.5 Bar. Consecutive steps over membrane cutoffs of 100 kD, 30 kD, 10 kD, and 5 kD were tested in different set-ups.

Generally, every filter step resulted in generation of about 5 to 10% of retentate, depending on the composition concentration of the filtered solutions. Three intermediate saccharide polymer preparations were generated this way, in the following called solutions 1, 2 and 3. All filtration steps were carried out in the original Buffer of extraneal, and buffer composition as well as pH was controlled throughout the workflow.

Solution 1 was generated from 80 Liters of Extraneal going through Pelicon Ultracel® 100 kD, 30 kD, 10 kD, 10 kD and was finally concentrated on a 5 kD Filter.

Solution 2 was generated running the same filter combination than for Solution 1, but in series, so filtration on a following filter started, before the previous filtration cycle was finalized. This save time but also reduced filtration efficacy.

Solution 3 was generated as solution 2, but this time the kD membrane was applied twice as a supplemental filter, before it was again applied to concentrate the intermediate saccharide polymer preparation.

The results show that comparative results can be obtained by very different methods.

All solutions were analyzed on their carbohydrate composition by gel permeation chromatography on a microsphere 60 SEC 5 μm column of the dimensions of 300*4.6 mm, at 1.2 ml/min at pressure between 5 and 200 bars. Chromatography was run with purified water. Icodextrin, 70 kD, 10 kD and kD Dextran molecular weight markers were run in parallel to identify the composition of the intermediate preparations. Carbohydrate concentration was measured by RI Detection. In summary, total Carbohydrate concentration corresponded to the area under the curve after background subtraction, following calibration established on Icodextrin, maltose and glucose standard solutions. Quantification of molecular weight size fractions was assessed using dextran molecular weight standards and Icodextrin as a comparative standard.

Results of the molecular weight composition of the fractions are given in tables 2 to 5. "MW" in the tables means "molecular weight". "Mw" means "weight average molecular weight".

TABLE 2

Composition of Extraneal applied to experimental preparation of intermediate saccharide polymer preparations: found Mw = 14.1 kD, Mn = 5.8 kD.

| MW fractions (KD) | Icodextrin Refr. Index | wt % | Sum % | mol number |
|---|---|---|---|---|
| 90 | 509 | 0.10 | 8.20 | 0.00 |
| 60 | 11967 | 2.42 | | 0.04 |
| 43 | 28061 | 5.67 | | 0.13 |
| 30 | 51254 | 10.37 | 10.37 | 0.35 |
| 18 | 63270 | 12.80 | 32.23 | 0.71 |
| 12.5 | 54053 | 10.93 | | 0.87 |
| 10.5 | 42056 | 8.50 | | 0.81 |
| 8.8 | 32712 | 6.62 | 28.35 | 0.75 |
| 7.5 | 26317 | 5.32 | | 0.71 |
| 6.6 | 22325 | 4.51 | | 0.68 |
| 5.8 | 20131 | 4.07 | | 0.70 |
| 5 | 19242 | 3.89 | | 0.78 |
| 4.3 | 19485 | 3.94 | | 0.92 |
| 3.9 | 22090 | 4.47 | 15.26 | 1.15 |
| 3.1 | 22263 | 4.50 | | 1.45 |
| 2.6 | 15558 | 3.15 | | 1.21 |
| 2.2 | 15558 | 3.15 | | 1.43 |
| 1.8 | 8578 | 1.73 | 4.01 | 0.96 |
| 1.5 | 6453 | 1.30 | | 0.87 |
| 1.2 | 4809 | 0.97 | | 0.81 |
| 0.987 | 3618 | 0.73 | 1.58 | 0.74 |
| 0.827 | 2716 | 0.55 | | 0.66 |
| 0.667 | 1098 | 0.22 | | 0.33 |
| 0.5 | 366 | 0.07 | | 0.15 |

TABLE 3

Composition of Solution 1 (Mw = 3.7 kD, Mn = 2.2 kD)

| MW fraction (KD) | Sol. 1 Refr. Index | wt % | Sum % | mol number |
|---|---|---|---|---|
| 90 | 71 | 0.07 | 0.46 | 0.00 |
| 60 | 171 | 0.16 | | 0.00 |
| 43 | 258 | 0.24 | | 0.01 |
| 30 | 434 | 0.40 | 0.40 | 0.01 |
| 18 | 787 | 0.73 | 3.30 | 0.04 |
| 12.5 | 1176 | 1.09 | | 0.09 |
| 10.5 | 1595 | 1.48 | | 0.14 |
| 8.8 | 2066 | 1.92 | 21.99 | 0.22 |
| 7.5 | 2616 | 2.43 | | 0.32 |
| 6.6 | 3260 | 3.03 | | 0.46 |
| 5.8 | 4080 | 3.79 | | 0.65 |
| 5 | 5139 | 4.77 | | 0.95 |
| 4.3 | 6525 | 6.06 | | 1.41 |
| 3.9 | 8686 | 8.06 | 45.99 | 2.07 |
| 3.1 | 12950 | 12.02 | | 3.88 |
| 2.6 | 13952 | 12.95 | | 4.98 |
| 2.2 | 13952 | 12.95 | | 5.89 |
| 1.8 | 6944 | 6.45 | 16.38 | 3.58 |
| 1.5 | 5705 | 5.30 | | 3.53 |
| 1.2 | 4995 | 4.64 | | 3.86 |
| 0.987 | 4686 | 4.35 | 11.47 | 4.41 |
| 0.827 | 4421 | 4.10 | | 4.96 |
| 0.667 | 2386 | 2.22 | | 3.32 |
| 0.5 | 858 | 0.80 | | 1.59 |

TABLE 4

Composition of solution 2: Mw = 6 kD, Mn = 3.7 kD

| MW fraction (KD) | Sol. 2 Refr. Index | wt % | Sum % | mol number |
|---|---|---|---|---|
| 90 | 428 | 0.05 | 0.44 | 0.00 |
| 60 | 1116 | 0.12 | | 0.00 |
| 43 | 2492 | 0.27 | | 0.01 |
| 30 | 6595 | 0.72 | 0.72 | 0.02 |
| 18 | 18651 | 2.04 | 11.73 | 0.11 |
| 12.5 | 35458 | 3.88 | | 0.31 |
| 10.5 | 53111 | 5.81 | | 0.55 |
| 8.8 | 67722 | 7.41 | 51.68 | 0.84 |
| 7.5 | 77730 | 8.51 | | 1.13 |
| 6.6 | 83814 | 9.17 | | 1.39 |
| 5.8 | 88351 | 9.67 | | 1.67 |
| 5 | 81734 | 8.94 | | 1.79 |
| 4.3 | 72866 | 7.97 | | 1.85 |
| 3.9 | 65137 | 7.13 | 24.20 | 1.83 |
| 3.1 | 57391 | 6.28 | | 2.03 |
| 2.6 | 49303 | 5.40 | | 2.08 |
| 2.2 | 49303 | 5.40 | | 2.45 |
| 1.8 | 32714 | 3.58 | 8.22 | 1.99 |
| 1.5 | 24700 | 2.70 | | 1.80 |
| 1.2 | 17689 | 1.94 | | 1.61 |
| 0.987 | 12407 | 1.36 | 3.00 | 1.38 |
| 0.827 | 8942 | 0.98 | | 1.18 |

TABLE 4-continued

Composition of solution 2: Mw = 6 kD, Mn = 3.7 kD

| MW fraction (KD) | Sol. 2 Refr. Index | wt % | Sum % | mol number |
|---|---|---|---|---|
| 0.667 | 4600 | 0.50 | | 0.75 |
| 0.5 | 1498 | 0.16 | | 0.33 |

TABLE 5

Composition of solution 3: Mw 3.5 kD, Mn = 2.1 kD

| MW fraction (KD) | Sol. 3 Refr. Index | wt % | Sum % | mol number |
|---|---|---|---|---|
| 90 | 225 | 0.12 | 0.53 | 0.00 |
| 60 | 347 | 0.19 | | 0.00 |
| 43 | 402 | 0.22 | | 0.01 |
| 30 | 505 | 0.28 | 0.28 | 0.01 |
| 18 | 709 | 0.39 | 1.79 | 0.02 |
| 12.5 | 1031 | 0.56 | | 0.04 |
| 10.5 | 1540 | 0.84 | | 0.08 |
| 8.8 | 2316 | 1.26 | 22.34 | 0.14 |
| 7.5 | 3474 | 1.89 | | 0.25 |
| 6.6 | 5119 | 2.79 | | 0.42 |
| 5.8 | 7281 | 3.97 | | 0.68 |
| 5 | 9923 | 5.41 | | 1.08 |
| 4.3 | 12862 | 7.01 | | 1.63 |
| 3.9 | 15763 | 8.60 | 39.92 | 2.20 |
| 3.1 | 18171 | 9.91 | | 3.20 |
| 2.6 | 19631 | 10.71 | | 4.12 |
| 2.2 | 19631 | 10.71 | | 4.87 |
| 1.8 | 17506 | 9.55 | 24.10 | 5.30 |
| 1.5 | 14674 | 8.00 | | 5.33 |
| 1.2 | 12016 | 6.55 | | 5.46 |
| 0.987 | 10043 | 5.48 | 11.04 | 5.55 |
| 0.827 | 7375 | 4.02 | | 4.86 |
| 0.667 | 2320 | 1.27 | | 1.90 |
| 0.5 | 513 | 0.28 | | 0.56 |

Example 3: Examples for Calculation of Mw and Mn for Different Osmotically Active Compositions

TABLE 6

Calculation of Mw and Mn of solution 3 (on the example of 5.75% concentration of saccharide polymer:

| M(ni) | MW(Mi)(kD) | g/L(ni*Mi) | g/L*MW(ni*Mi²) |
|---|---|---|---|
| 0.001 | 90 | 0.07 | 6.3 |
| 0.002 | 60 | 0.11 | 6.5 |
| 0.003 | 43 | 0.13 | 5.4 |
| 0.005 | 30 | 0.16 | 4.7 |
| 0.012 | 18 | 0.22 | 4.0 |
| 0.026 | 12.5 | 0.32 | 4.0 |
| 0.046 | 10.5 | 0.48 | 5.1 |
| 0.083 | 8.8 | 0.73 | 6.4 |
| 0.145 | 7.5 | 1.09 | 8.2 |
| 0.243 | 6.6 | 1.61 | 10.6 |
| 0.394 | 5.8 | 2.28 | 13.2 |
| 0.622 | 5 | 3.11 | 15.6 |
| 0.938 | 4.3 | 4.03 | 17.3 |

TABLE 6-continued

Calculation of Mw and Mn of solution 3 (on the example of 5.75% concentration of saccharide polymer:

| M(ni) | MW(Mi)(kD) | g/L(ni*Mi) | g/L*MW(ni*Mi²) |
|---|---|---|---|
| 1.267 | 3.9 | 4.94 | 19.3 |
| 1.838 | 3.1 | 5.70 | 17.7 |
| 2.368 | 2.6 | 6.16 | 16.0 |
| 2.798 | 2.2 | 6.16 | 13.5 |
| 3.050 | 1.8 | 5.49 | 9.9 |
| 3.067 | 1.5 | 4.60 | 6.9 |
| 3.140 | 1.2 | 3.77 | 4.5 |
| 3.191 | 0.987 | 3.15 | 3.1 |
| 2.796 | 0.827 | 2.31 | 1.9 |
| 1.091 | 0.667 | 0.73 | 0.5 |
| 0.322 | 0.5 | 0.16 | 0.1 |
| Sums 27.447 | | 57.50 | 200.8 |

For each fraction i, the concentration in Mol is taken as value for compound molecule number (ni) of such a fraction, and the mean molecular weight of the fraction is accounted for as the molecular weight Mi of all molecules of that fraction. Then we can establish the sums $\Sigma(ni)=27.5$, $\Sigma(ni*Mi)=57.5$, and $\Sigma(ni*Mi^2)=200.8$, and calculate $Mw=\Sigma(ni*Mi^2)/\Sigma(ni*Mi)=3.49$ kD, as well as $Mn=\Sigma(ni*Mi)/\Sigma(ni)=2.09$ kD.

Calculate Mw and Mn of glycerol (1% solution):

| M(ni) | MW(Mi) (kDalton) | g/L(ni*Mi) | g/L*MW(ni*Mi²) |
|---|---|---|---|
| 29 | 0.342 | 10 | 3.42 |

A fraction of 1% maltose corresponds to a single fraction of a concentration of 29M (ni), of a molecular weight of 0.342 kD, resulting in $\Sigma(ni)=ni=29$, $\Sigma(ni*Mi)=niMi=10$, and $\Sigma(ni*Mi^2)=niMi^2=3.42$.

Calculate Mw and Mn of a composition of 5.75% saccharide polymers of sol 3 and 1% maltose $$\begin{aligned}
Mw &= \Sigma(ni^*Mi^2)/\Sigma(ni^*Mi) \\
&= [\Sigma Sol3(ni^*Mi^2) + [\Sigma mal(ni^*Mi^2)]/ \\
&\quad [^2)/\Sigma Sol3\ (ni^*Mi) + \Sigma mal\ (ni^*Mi)] \\
&= (200.8 + 3.42)/(57.5 + 10) \\
&= 3.03
\end{aligned}$$

$$\begin{aligned}
Mn &= \Sigma(ni^*Mi)/\Sigma(ni) \\
&= [\Sigma Sol3(ni^*Mi) + [\Sigma mal(ni^*Mi)]/ \\
&\quad [\Sigma Sol3(ni) + \Sigma mal(ni)] \\
&= (57.5 + 10)/(27.4 + 29) \\
&= 1.19
\end{aligned}$$

TABLE 7

Calculate Mw and Mn of a 1% amino acid mix

| component | M(ni) | MW(Mi)(kDalton) | g/L(ni*Mi) | g/L*MW(ni*Mi²) |
|---|---|---|---|---|
| Adenine | 0.77719 | 0.135 | 0.105 | 0.0142 |
| L-Alanine | 4.85591 | 0.089 | 0.432 | 0.0385 |

TABLE 7-continued

Calculate Mw and Mn of a 1% amino acid mix

| component | M(ni) | MW(Mi)(kDalton) | g/L(ni*Mi) | g/L*MW(ni*Mi$^2$) |
|---|---|---|---|---|
| L-Arginine HCl | 2.45793 | 0.174 | 0.428 | 0.0744 |
| L-Asparagine | 3.23999 | 0.132 | 0.428 | 0.0565 |
| L-Aspartic Acid | 3.21563 | 0.133 | 0.428 | 0.0569 |
| L-Cysteine HCl | 3.53454 | 0.121 | 0.428 | 0.0517 |
| Glutamine | 2.92931 | 0.146 | 0.428 | 0.0624 |
| L-Glutamic Acid | 2.90938 | 0.147 | 0.428 | 0.0629 |
| Glycine | 5.70239 | 0.075 | 0.428 | 0.0321 |
| L-Histidine HCl | 2.75922 | 0.155 | 0.428 | 0.0663 |
| Myo-Inositol | 2.37600 | 0.18 | 0.428 | 0.0770 |
| L-Isoleucine | 3.26473 | 0.131 | 0.428 | 0.0560 |
| L-Leucine | 6.61336 | 0.131 | 0.866 | 0.1135 |
| L-Lysine HCl | 2.92931 | 0.146 | 0.428 | 0.0624 |
| L-Methionine | 2.87033 | 0.149 | 0.428 | 0.0637 |
| Para-Amino-benzoic Acid | 0.31363 | 0.137 | 0.043 | 0.0059 |
| L-Phenylalanine | 2.59200 | 0.165 | 0.428 | 0.0706 |
| L-Proline | 3.71895 | 0.115 | 0.428 | 0.0492 |
| L-Serine | 4.07314 | 0.105 | 0.428 | 0.0449 |
| L-Threonine | 3.59394 | 0.119 | 0.428 | 0.0509 |
| L-Tryptophan | 2.09647 | 0.204 | 0.428 | 0.0872 |
| L-Tyrosine | 2.36287 | 0.181 | 0.428 | 0.0774 |
| L-Valine | 3.65538 | 0.117 | 0.428 | 0.0500 |
| Uracil | 3.81856 | 0.112 | 0.428 | 0.0479 |
| Sum | 76.66016 |  | 10.000 | 1.3725 |

For each fraction i, the concentration in Mol is taken as value for compound molecule number (ni) of such a fraction, and the molecular weight of the corresponding amino acid is accounted for as Mi. Then we can establish the sums $\Sigma(ni)=76.7$, $\Sigma(ni*Mi)=10$, and $\Sigma(ni*Mi^2)=1.37$, and calculate $Mw=\Sigma(ni*Mi^2)/\Sigma(ni*Mi)=0.137$ kD, as well as
$Mn=\Sigma(ni*Mi)/\Sigma(ni)=0.130$ kD.

Calculate Mw and Mn of a composition of 5.75% saccharide polymers of sol 3 and 1% amino acid mix $$Mw = \sum (ni^*Mi^2) / \sum (ni^*Mi) =$$
$$\left[\sum Sol3(ni^*Mi^2) + \sum aam(ni^*Mi^2)\right] / \left[\sum Sol3(ni^*Mi) + \sum aam(ni^*Mi)\right] = (200.8 + 1.4)/(57.5 + 10) = 3.00$$
$$Mn = Mn = \sum (ni^*Mi) / \sum (ni) = \left[\sum Sol3(ni^*Mi) + \sum aam(ni^*Mi)\right] / \left[\sum Sol3(ni) + \sum aam(ni)\right] =$$
$$(57.5 + 10)/(27.4 + 76.7) = 0.75$$

Example 4: Osmolality of Claimed Osmotically Active Compositions in Physiological Buffer Intermediate saccharide polymer preparations 1 and 3 from example 2 were measured for osmolality at different concentrations in presence of 0,1, 2 and 4% maltose, using the freezing point method, on an OSMOMAT 030 Gonotec Cryoscopic Osmometer. (results in mOsmol/kg). In all cases a higher osmolality as compared to Icodextrin was found.
Experimental Results:
All intermediate preparations, preparations and solutions of such preparations were continuously kept in 1×Buffer (5.4 g/l NaCl, 4.5 g/l Na-lactate, 0.257 g/l CaCl$_2$, and 0.051 g/l MgCl$_2$, at pH5.5. Maltose was added to intermediate saccharide polymer preparations at different concentrations. Therefore, variations in osmolality are solely due to variation of concentration of intermediate saccharide polymer preparations tables (8 to 11).

TABLE 8

Compositions w/o Maltose Addition

Intermediate polymer preparation w/o maltose

| | | intermediate prep | | |
|---|---|---|---|---|
| % total CHO | % | Sol 1 | Sol 3 | ICO |
| 7.50% | 7.50% | | | 284 |
| 6.80% | 6.75% | 311 | | |
| 5.75% | 5.75% | 308 | 303 | |
| 4.80% | 4.80% | 305 | 298 | |
| 3.90% | 3.90% | 303 | 295 | |
| 3% | 3% | 295 | 293 | |

TABLE 9

Compositions with 1% Maltose

Intmediate Polymer preparation + 1% Maltose

| | | intermediate prep | | |
|---|---|---|---|---|
| % total CHO | % | Sol 1 | Sol 3 | ICO |
| 8.50% | 7.50% | | | 315 |
| 7.80% | 6.80% | 343 | | |
| 6.75% | 5.75% | 334 | 329 | |
| 5.80% | 4.80% | 331 | 327 | |
| 4.90% | 3.90% | 330 | 326 | |
| 4% | 3% | 326 | 322 | |

TABLE 10

Compositions with 2% Maltose
Intmediate Polymer preparation + 2% Maltose

| | | intermediate prep | | |
|---|---|---|---|---|
| % total CHO | % | Sol 1 | Sol 3 | ICO |
| 9.50% | 7.50% | | | 350 |
| 8.80% | 6.80% | 373 | | |
| 7.75% | 5.75% | 373 | 363 | |
| 6.80% | 4.80% | 366 | 359 | |
| 5.90% | 3.90% | 361 | 356 | |
| 5% | 3% | 360 | 355 | |

TABLE 11

Compositions with 4% Maltose
Intmediate Polymer preparation + 4% Maltose

| | | intermediate prep | | |
|---|---|---|---|---|
| % total CHO | % | Sol 1 | Sol 3 | ICO |
| 11.50% | 7.50% | | | 409 |
| 10.80% | 6.80% | 433 | | |
| 9.75% | 5.75% | 431 | 416 | |
| 8.80% | 4.80% | 427 | 417 | |
| 7.90% | 3.90% | 418 | 415 | |
| 7% | 3% | 417 | 410 | |

Obtained experimental results were normalized and extrapolated to estimate osmolalilties for the three solutions over the range of concentrations claimed by this application (tables 12-15).

Normalized and extrapolated osmolalities for solutions of this invention

TABLE 12

Compositions w/o Maltose Addition
Interm. polymer prep w/o maltose

| 0% maltose | | intermediate prep | |
|---|---|---|---|
| % total CHO | % | Sol 1 | Sol 3 |
| 6.80% | 6.80% | 311-312 | 306-308 |
| 5.75% | 5.75% | 307-309 | 302-304 |
| 4.80% | 4.80% | 304-305 | 298-299 |
| 3.90% | 3.90% | 301-303 | 294-296 |
| 3% | 3% | 295-297 | 292-293 |
| 2% | 2% | 292-294 | 287-289 |

TABLE 13

Compositions with 1% Maltose
Interm. polymer prep with 1% maltose

| 1% maltose | | intermediate prep | |
|---|---|---|---|
| % total CHO | % | Sol 1 | Sol 3 |
| 6.75% | 5.75% | 335-337 | 330-332 |
| 5.80% | 4.80% | 332-334 | 327-329 |
| 4.90% | 3.90% | 328-330 | 323-325 |
| 4% | 3% | 325-327 | 320-322 |
| 3% | 2% | 321-323 | 316-318 |
| 2% | 1% | 318-320 | 313-315 |

TABLE 14

Compositions with 2% Maltose
Intm. Polymer prep + 2% Maltose

| 2% maltose | | intermediate prep | |
|---|---|---|---|
| % total CHO | % | Sol 1 | Sol 3 |
| 6.80% | 4.80% | 366-368 | 359-361 |
| 5.90% | 3.90% | 362-364 | 356-358 |
| 5% | 3% | 359-361 | 352-354 |
| 4% | 2% | 356-358 | 349-351 |
| 3% | 1% | 352-354 | 346-348 |

TABLE 15

Compositions with 4% Maltose
Intm. Polymer prep + 4% Maltose

| 4% maltose | | intermediate prep | |
|---|---|---|---|
| % total CHO | % | Sol 1 | Sol 3 |
| 7% | 3% | 418-420 | 409-411 |
| 6% | 2% | 415-417 | 406-408 |
| 5% | 1% | 412-414 | 402-404 |

Those skilled in the art understand that other solutions may be prepared with intermediate saccharide polymer preparations of lower Mw, Mn, than solutions 1 and 3. Such solutions would show higher osmolalities at comparable concentrations up to 500 mOsmol/kg, in presence of 4% maltose.

We also measured osmolalities of Solution 3 saccharide polymers 5.75% and Icodextrin 7.5%, both in physiological buffer, adding 1% of an amino acid mix (composition see example 3), maltose, sucrose, glucose, glycerol, carnitine, or carnisol (Table 16).

TABLE 16

Osmolalities of other small molecular weight osmotic drivers in comparison to maltose (at 1%) added to solution 3 (5.75 ù or Icodextrin 7.5%):

| | no add | 1% aam | 1% mal | 1% suc | 1% glu | 1% gly | 1% cami | 1% carno | |
|---|---|---|---|---|---|---|---|---|---|
| Sol3 glucans (5.15%) | 308 | 382 | 340 | 341 | 366 | 410 | 396 | 357 | mOsm/L |
| Icodextrin (7.5%) | 284 | 354 | 305 | 301 | 328 | 402 | 367 | 318-348 | mOsm/L |

Example 5: Assessing Ultrafiltration and CHO Absorption in an Animal Model

Peritoneal dialysis dwell times vary from less than 2 hours, for example in automated peritoneal dialysis (ADP): over 4 to 6 hours, for example in continuous ambulatory peritoneal dialysis (CAPD); to 8 to 12 hours in long dialysis dwells, for example whole day or whole night dwells. In this application, dwells of up to 6 hours are referred to as short PD dwells, whereas dwells of 8 hours and longer are referred to as long dwells.

One of our saccharide polymer preparations (Solution 3, at 5.75 wt-% glucan) was supplemented with 1% maltose to give solution 4 (example 3, Mw=3.03 kD, Mn=1.19 kD) at a total CHO concentration of 6.75% M, and an osmolality of 329 mOsmol/kg, and was applied to the rabbit model described by Leypoldt et al. (2013, PDI Vol. 33, pp 124-131), in comparison to commercial Extraneal® containing 7.5% Icodextrin. 6 rabbits were separated into two groups A and B. The two solutions were tested on both groups in the frame of a cross over study.

Leypoldt et al. had been calculating ultrafiltration after a single dwell of 240 minutes, correcting for resting volume with a fluorescent volume marker. Instead, we carried out 5 dwells a day at 3, 30, 60, 120 and 240 minutes. The 3 minutes dwell served as a pre-flushing dwell to occupy volume that cannot be recovered from the peritoneum in a single dwell, and to guaranty that only fresh PD fluid is present in the peritoneum for the 30 minutes dwell. Further dwells were run consecutively through the day. At the end of each dwell, dialysate was recovered, and weighted to establish dialysate volume and to calculate net ultrafiltration volume. Samples of every dialysate were submitted to measure total CHO concentrations. Methods for CHO quantification as described in example 2. Altogether 6 rabbits were submitted to dialysis comparing an experimental dialysis solution corresponding to this invention with Icodextrin. 3 rabbits started with the test solution, the other 3 rabbits started with the Icodextrin control solution. After 2 days dialysis, rabbits were let to recover for two days, before being switched to the other dialysis solution respectively. All together 96 dialysis dwells were run, 16 dwells on each rabbit. We did not observe difference of dwell volumes depending on which solution a rabbit started on. For statistical evaluation we applied a single sided t-test with independent variances for both tested groups. Every dwell was regarded as an independent event and no correction for multiple testing was carried out. Table 17 shows results on net ultrafiltration volumes (in ml) for each dwell. (* statistically significance at <5%).

TABLE 17

NUF comparisons at different dwell times.

|  | NUF (ml) Test Sol.4 | NUF (ml) Icodextrin | pval |
| --- | --- | --- | --- |
| 30 min | 9 (±18) | −2 (±6) | 0.063 |
| 60 min | 34 (±13) | 12 (±8) | 0.001* |
| 120 min | 46 (±13) | 13 (±14) | 0.002* |
| 240 min | 50 (±8) | 28 (±21) | 0.011* |

TABLE 18

Average CHO absorption and calculation of NUF/CHO ratios, comparing 2 Solutions at different dwell times. Average CHO absorptions and NUF/CHOabs ratios are calculated in table 18

|  | NUF(ml) Test sol.4 | NUF (ml) Ico | CHOabs. Test (g) | CHOabs. Ico (g) | NUF/CHO Test | NUF/CHO Ico |
| --- | --- | --- | --- | --- | --- | --- |
| 30 min | 9 | −2 | 3.88 | 3.69 | 2.4 | −0.5 |
| 60 min | 34 | 12 | 4.18 | 3.58 | 8.1 | 3.3 |
| 120 min | 46 | 13 | 5.15 | 4.78 | 9.0 | 2.7 |
| 240 min | 50 | 28 | 5.85 | 4.75 | 8.6 | 5.9 |

In summary, we found:
an average NUF of 9.3 ml/120 ml for a solution on the basis of this invention, after a 30 minutes dwell, versus −2 ml/120 ml for Extraneal.
an average NUF of 34 ml/120 ml for our composition after a 60 minutes dwell, versus 12.3 ml/120 ml for Extraneal.
an average NUF of 46 ml/120 ml for our composition after a 120 minutes dwell, versus 13 ml/120 ml for Extraneal.
an average NUF of 50 ml/120 ml for our composition after a 240 minutes dwell, versus 28 ml/120 ml for Extraneal.

These results were very surprising to us. Based on data reported by Leypoldt et al. we would have expected NUF values around 50 ml/120 ml for Extraneal at 20 min. Most likely minor differences in realization of the model, the fact that we worked with 4 real dwells through the day, instead of a single dwell, and that we only considered the volume recovered from the rabbits, without corrections for resting volumes after the dwell, accounts for this difference. On the other hand resting volumes should be less of an issue in our study since we did multiple dwells during a day. Nevertheless, the comparatively higher performance of our composition versus Icodextrin at all time points, but more drastical at time points 60, 120 and 240 of this model, corresponding to short dwells in humans, by far exceeded our expectations. The model indicates that our compositions, even at lower concentrations then those applied in this animal experiment, would be highly efficient osmotic drivers for any medical application in general and for peritoneal dialysis specifically.

Furthermore, the ration NUF/CHO abs. is higher for the test solution at every time point. More importantly the three best values for this ration are all for the test solution, event at 240 min, which had previously been characterized to correspond to a long dwell.

The invention claimed is:
1. A liquid aqueous composition, comprising water and a composition comprising components a) to d):
a) maltose in a content of 5 to 75 wt-% of the total weight of a)-d), b) glucose in a content of less than ½ the content of a), and in a total content of less than 5 wt-% of the total weight of a)-d),
c) glucan molecules of DP 3 and DP 4, taken together, in a content of less than ½ of the content of a),
d) glucan molecules of DP>4 in a content to give 100 wt-% together with a), b) and c), wherein
  glucan molecules of DP>10 are present in an amount of 15-80 wt-% of the total weight of a)-d),
  glucan molecules of DP>24 are present in an amount of 2-60 wt-% of the total weight of a)-d),
  glucan molecules of DP>55 are present in an amount of less than 15 wt-% of the total weight of a)-d).
wherein the liquid aqueous composition has an osmolality of 290 to 420 mOsm/kg.

2. The composition of claim 1, wherein the weight average molecular weight of a)-d), taken together, is Mw 0.8-15 kD and the number average molecular weight of a)-d), taken together, is Mn 0.2-3 kD.

3. The composition of claim 1, wherein glucan molecules of DP>111 are present in an amount of less than 1.5 wt-%.

4. The composition of claim 1, wherein glucan molecules of DP>246 are present in an amount of less than 0.6 wt-%.

5. The composition of claim 1, wherein glucan molecules of DP>10 are present in an amount of 20-80 wt-%.

6. The composition of claim 1, wherein glucan molecules of DP>10 are present in an amount of 35-80 wt-%.

7. The composition of claim 1, comprising the glucose in a content of less than ⅓ the content of a).

8. The composition of claim 1, comprising the glucose in a content of at least 0.1 wt-%.

9. The composition of claim 1, comprising the glucan molecules of DP 3 and DP 4, taken together, in a content of less than ⅓ of the content of a).

10. The composition of claim 1, comprising the glucan molecules of DP 3 and DP 4, taken together, in a content of at least 0.1 wt-%.

11. The composition of claim 1, comprising the compound a), or mixture of compounds of a) in a content of 8 to 65 wt-%.

12. The composition of claim 1, comprising the glucan molecules of DP>4 in a content of more than 16 wt-% of the total weight of a)-d).

13. The composition of claim 1, wherein the glucan molecules are derivatized.

14. The liquid aqueous composition of claim 1, having an osmolality of 290 to 350 mOsm/kg.

15. The composition according to claim 1,
wherein the composition is a peritoneal therapeutic fluid or solution; a dialysis fluid or solution; a peritoneal dialysis fluid or solution; a gastroenterological solution; a nutritional solution; a nutritional infusion; a drug administration solution; a detoxifying solution; a physiological substitute or additive preparation; a physiological substitute or additive preparation for physiological body fluids; a physiological substitute or additive preparation for blood, plasma, serum or interstitial body fluids; an adhesion reducing solution after surgery; a solution for clyster; a laxative; an osmotic agent an infant dietetic; an agent with reduced cytotoxicity, or a treatment for a renal disease.

16. A method for producing a liquid aqueous composition according to claim 11, the method comprising the steps of:
  preparing an aqueous solution of starch, having a solids content of from 10 wt-% to 60 wt-%; gelatinization, by treating said solution successively with a specific combination of enzymes selected from the group consisting of an amyloglucosidase and an amylase;
  purifying the solution;
  fractionating the solution in such a way as to eliminate or decrease molecular weight saccharide fractions having a molecular weight higher than 40000 D and to recover the other fractions;
  adding maltose, and optionally glucose wherein the liquid aqueous composition is obtained.

17. A container or kit comprising at least one compartment containing the composition of claim 1.

18. The composition according to claim 1, having an osmolality of 320 to 340 mOsm/kg.

19. A method of treating renal disease in a human comprising administering the composition according to claim 1 to the human.

20. The composition according to claim 1, wherein glucose is at a concentration of less than 0.2% w/v of the liquid aqueous composition.

* * * * *